(12) United States Patent
Chung et al.

(10) Patent No.: US 9,914,743 B2
(45) Date of Patent: Mar. 13, 2018

(54) ORGANIC SILVER COMPLEXES, THEIR PREPARATION METHODS AND THEIR METHODS FOR FORMING THIN LAYERS

(71) Applicant: Inktec Co., Ltd., Ansan (KR)

(72) Inventors: Kwang-Choon Chung, Seoul (KR); Hyun-Nam Cho, Gunpo (KR); Myoung-Seon Gong, Seoul (KR); Yi-Sup Han, Goyang (KR); Jeong-Bin Park, Ansan (KR); Dong-Hun Nam, Seoul (KR); Seong-Yong Uhm, Suwon (KR); Young-Kwan Seo, Siheung (KR)

(73) Assignee: Inktec Co., Ltd., Kyeongki-do (KR)

( * ) Notice: Subject to any disclaimer, the term of this patent is extended or adjusted under 35 U.S.C. 154(b) by 85 days.

(21) Appl. No.: 15/071,593

(22) Filed: Mar. 16, 2016

(65) Prior Publication Data
US 2016/0194339 A1    Jul. 7, 2016

Related U.S. Application Data

(60) Division of application No. 14/060,079, filed on Oct. 22, 2013, now abandoned, which is a continuation of
(Continued)

(30) Foreign Application Priority Data

| Feb. 7, 2005 | (KR) | ......................... 10-2005-0011478 |
| Feb. 11, 2005 | (KR) | ......................... 10-2005-0011631 |
| Feb. 6, 2006 | (KR) | ......................... 10-2006-0011083 |

(51) Int. Cl.
*C23C 18/08* (2006.01)
*C07F 1/00* (2006.01)
(Continued)

(52) U.S. Cl.
CPC .............. *C07F 1/00* (2013.01); *C07C 211/65* (2013.01); *C07C 271/02* (2013.01); *C07F 1/005* (2013.01);
(Continued)

(58) Field of Classification Search
CPC ...................................................... C23C 18/08
See application file for complete search history.

(56) References Cited

U.S. PATENT DOCUMENTS

| 3,146,130 A | 8/1964 | Kroger et al. |
| 3,979,382 A | 9/1976 | Martinez-Alvarez et al. |

(Continued)

FOREIGN PATENT DOCUMENTS

| CA | 2575862 A1 | 2/2006 |
| GB | 609807 | 10/1948 |

(Continued)

OTHER PUBLICATIONS

Bernard et al., "Effect of heating on metallic carbamates. III. Silver carbamate", Bulletin de la Societe Chimique de France, 1970, pp. 2938-2940, 8-9.

(Continued)

*Primary Examiner* — Robert A Vetere
(74) *Attorney, Agent, or Firm* — The Webb Law Firm

(57) ABSTRACT

Provided herein is a method for preparing a silver complex. The method includes reacting a silver oxide with a mixture of ammonium carbamate and isopropyl amine at room temperature in the presence of methanol.

1 Claim, 14 Drawing Sheets

Related U.S. Application Data application No. 13/469,412, filed on May 11, 2012, now Pat. No. 8,679,242, which is a continuation of application No. 11/815,745, filed as application No. PCT/KR2006/000451 on Feb. 7, 2006, now Pat. No. 8,226,755.

(51) Int. Cl.

| | | |
|---|---|---|
| *C07C 271/02* | (2006.01) | |
| *C07C 211/65* | (2006.01) | |
| *C09D 5/24* | (2006.01) | |
| *C09D 11/30* | (2014.01) | |
| *C09D 11/52* | (2014.01) | |
| *C25D 3/46* | (2006.01) | |
| *H05K 3/10* | (2006.01) | |

(52) U.S. Cl.
CPC ............. *C09D 5/24* (2013.01); *C09D 11/30* (2013.01); *C09D 11/52* (2013.01); *C23C 18/08* (2013.01); *C25D 3/46* (2013.01); *H05K 3/105* (2013.01)

(56) References Cited

U.S. PATENT DOCUMENTS

| | | | |
|---|---|---|---|
| 4,405,360 | A | 9/1983 | Cardarelli |
| 4,542,214 | A | 9/1985 | Bechara |
| 4,652,465 | A * | 3/1987 | Koto ............... B22F 1/025 |
| | | | 106/1.18 |
| 5,534,312 | A | 7/1996 | Hill et al. |
| 5,705,661 | A | 1/1998 | Iwakura et al. |
| 5,908,806 | A | 6/1999 | Kharas |
| 7,691,294 | B2 | 4/2010 | Chung et al. |
| 8,226,755 | B2 | 7/2012 | Chung et al. |
| 8,679,242 | B2 | 3/2014 | Chung et al. |
| 2004/0138362 | A1 | 7/2004 | Kim |
| 2004/0191423 | A1 | 9/2004 | Ruan et al. |
| 2005/0123621 | A1 * | 6/2005 | Burton ............... A61K 31/28 |
| | | | 424/618 |
| 2006/0011912 | A1 | 1/2006 | Park et al. |
| 2006/0035039 | A1 | 2/2006 | Ylitalo et al. |
| 2008/0206488 | A1 | 8/2008 | Chung et al. |
| 2008/0277381 | A1 | 11/2008 | Chung et al. |

FOREIGN PATENT DOCUMENTS

| | | |
|---|---|---|
| JP | 60243277 A | 5/1984 |
| JP | 2005530348 A | 10/2005 |
| JP | 2008509738 T | 4/2008 |
| JP | 2008531810 T | 8/2008 |
| JP | 2008534789 T | 8/2008 |
| KR | 100525846 B1 | 6/2004 |
| WO | 2006093398 A1 | 9/2006 |

OTHER PUBLICATIONS

Bernard et al., "Thermochemical study of some carbamates", Bulletin de la Societe Chimique de France, 1968, pp. 2362-2366, 6.
Binnemans et al., "Structure and Mesomorphism of Silver Alkanoates", Chem. Mater., 2004, pp. 2021-2027, vol. (16) No. 10.
Edwards et al., "Silver(I) carboxylates—II Some complexes of silver(I) acetate[1]", J. Inorg. Nucl. Chem., 1978, pp. 1599-1601, vol. (40).
George et al., "Chemically Reversible Organogels: Aliphatic Amines as "Latent" Gelators with Carbon Dioxide", J. Am. Chem. Soc., 2001, pp. 10393-10394, vol. 123(42).
George et al., "Chemically Reversible Organogels via "Latent" Gelators. Aliphatic Amines with Carbon Dioxide and Their Ammonium Carbamates", Langmuir, 2002, pp. 7124-7135, vol. 18.
Hermann, "Silver, Silver Compounds, and Silver Alloys", Ullmanns Encyclopedia of Ind. Chem., 1993, pp. 107-163, vol. (A24).
Jaber et al. "Crystal structure of ammine silver(I) p-nitrobenzoate", Eur. J. Solid State Inorg. Chem., 1995, pp. 25-33, vol. (32).
Katchalski et al., "The Chemical Structure of Some Diamine Carbamates", JACS, 1951, pp. 1829-1831, vol. 73(4).
Liebnitz et al., "Inhaltsstoffe Technischer Fettamingemische aus PO-Fettsauren", Journal fur Praktische Chemie, Dec. 1959, pp. 217-231, vol. 9.
Oldham, "Complexes of Simple Carboxylic Acids", Prog. Inorg. Chem., 1968, pp. 223-258, vol. (10).
Song et al., "A Model for an Intermediate on the Reaction Coordinate in Electron Transfer", Ang. Chem. Int. Ed. Engl., 1992, pp. 770-772, vol. (31) No. 6.
Sztyk et al., "CVD of AgI Complexes with Tertiary Phosphines and Perfluorinated Carboxylates—A New Class of Silver Precursors", Chem. Vapor Deposition, 2001, pp. 111-116, vol. (7).
Thomas et al., "Anisotropic Semiconduction in Single Crystals of Dichlorodiamminepalladium (II)-tetrachlorodiamminepalladium(IV) and Related Halogenbridged Mixed-valence Complexes", Journal of Chem. Soc. (A), 1971, pp. 512-515.
Whitcomb et al., "The molecular structure of [bis-triphenylphosphine-silver(I) stearate], [((C6H5)3P)2AG(O2C(CH2) 16CH3)], solubilization of long alkyl chain silver carboxylates", J. Chem. Cryst., 1996, pp. 99-105, vol. (26) No. 2.
Wright et al., "Reactions of Aralkyl Amines with Carbon Dioxide", JACS, 1948, pp. 3865-3866, vol. 70(11).

* cited by examiner

ORGANIC SILVER COMPLEXES, THEIR PREPARATION METHODS AND THEIR METHODS FOR FORMING THIN LAYERS

CROSS REFERENCE TO RELATED APPLICATIONS

This application is a divisional application of U.S. patent application Ser. No. 14/060,079, filed Oct. 22, 2013, which is a continuation of U.S. patent application Ser. No. 13/469,412 filed May 11, 2012, which is a continuation of U.S. patent application Ser. No. 11/815,745, filed Aug. 7, 2007, which is the National Stage of PCT/KR2006/000451, filed Feb. 7, 2006, and claims priority to Korean Patent Application No. 10-2005-011478, filed Feb. 7, 2005, Korean Patent Application No. 10-2005-0011631, filed Feb. 11, 2005, and Korean Patent Application No. 10-2006-0011083, filed Feb. 6, 2006, the disclosures of each of which are incorporated herein by reference in their entireties.

TECHNICAL FIELD

The present invention relates to a novel organic silver complex prepared by reacting a silver compound with an ammonium carbamate compound or an ammonium carbonate compound and a preparation method thereof.

BACKGROUND ART

According to Ullmann's Encyclopedia of Ind. Chem., Vol. A24, 107(1993), silver is a precious metal resistant to oxidation, with superior electrical and thermal conductivity and catalytic and antibiotic activity. Thus, silver and silver compounds are widely used in alloys, plating, medicine, photography, electricity and electronics, fibers, detergents, household appliances, and so forth.

Silver compounds can be used as catalyst in synthesis of organic compounds and polymers. Especially, with the recent regulation of use of lead in electric and electronic circuits, use of silver in low-resistance metal wirings, printed circuit boards (PCB), flexible printed circuit boards (FPC), antennas for radio frequency identification (RFID) stags, plasma display panels (PDP), liquid crystal displays (TFT-LCD), organic light emitting diodes (OLED), flexible displays and organic thin-film transistors (OTFT) as metal patterns or electrodes is on the increase.

Mostly, silver is used in the form of a paste comprising silver powder, a binder and a solvent. Or, a silver compound such as silver nitrate is reacted with another compound in an aqueous solution or an organic solvent to obtain a variety of silver compounds or organic silver compounds containing nanoparticles. These organic silver compounds are used to form metal patterns by chemical vapor deposition (CVD), plasma vapor deposition, sputtering, electroplating, photolithography, electron beam technique, laser technique, etc.

The most common coordinator for organic silver complexes is carboxylic acid (*Prog. Inorg. Chem.*, 10, p. 233 (1968)). However, because silver-containing metal carboxylate complexes are generally sensitive to light, hardly soluble in organic solvents (*J. Chem. Soc.*, (A)., p. 514 (1971), U.S. Pat. No. 5,534,312 (Jul. 9, 1996)) and have a high decomposition temperature, they are limited in application in spite of easiness in preparation. To solve this problem, several methods have been proposed in *J. Inorg. Nucl. Chem.*, 40, p. 1599 (1978), *Ang. Chem., Int. Ed. Engl.*, 31, p. 770 (1992), *Eur. J. Solid State Inorg. Chem.*, 32, p. (1995), *J. Chem. Cryst.*, 26, p. 99 (1996), *Chem. Vapor Deposition*, 7, 111 (2001), *Chem. Mater.*, 16, 2021 (2004), U.S. Pat. No. 5,705,661 (Jan. 6, 1998) and Korean Patent No. 2003-0085357 (Nov. 5, 2003). Among them are the methods of using carboxylic acid compounds having long alkyl chains or including amine compounds or phosphine compounds. However, the silver derivatives known thus far are limited and have insufficient stability or solubility. Moreover, they have a high decomposition temperature to be applied for pattern formation and are decomposed slowly.

U.K. Patent No. 609,807 published in 1948 discloses a method of reacting ammonium carbonate or ammonium carbamate with a transition metal salt to obtain a transition metal salt coordinated by ammonia as carbon dioxide is generated. The patent mentions that silver complexes coordinated by ammonia can be prepared by the method. However, surprisingly, the present inventors found out that when ammonium carbonate or ammonium carbamate is added to a silver compound such as silver oxide, a stable silver complex is obtained without generation of carbon dioxide. They also confirmed that the silver complex is isolated as solid and can be easily prepared into thin film.

The silver complexes of the present invention are characterized in that, because they can be prepared under various reaction conditions, they have superior stability and solubility, can be easily prepared into thin film, thus enabling ease metal patterning, and are decomposed at low temperature, thus being easily prepared into thin film or powder.

DISCLOSURE OF THE INVENTION

It is an object of the present invention to provide a novel organic silver complex obtained by reacting a silver compound with an ammonium carbamate compound or an ammonium carbonate compound and a preparation method thereof.

It is another object of the present invention to provide a novel organic silver complex having superior stability and solubility and being easily prepared into thin film and a preparation method thereof.

It is still another object of the present invention to provide a novel organic silver complex which enables formation of high-purity metal film since it is decomposed at low temperature and a preparation method thereof.

BEST MODE FOR CARRYING OUT THE INVENTION

Figure 1:
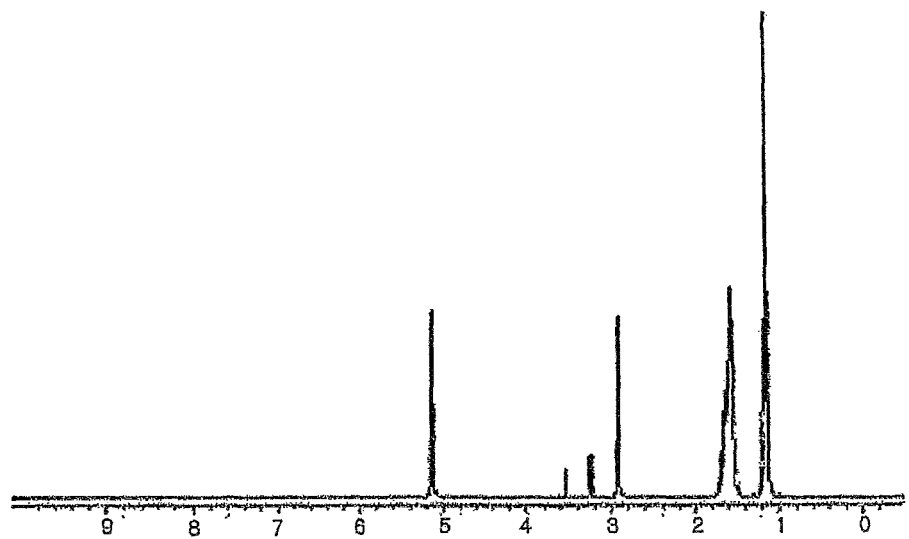
FIG. 1 is the $^1$H NMR spectrum of the silver complex of Example 1.

In order to attain the objects, the present inventors invented novel organic silver complexes by reacting the silver compound represented by the formula 2 below with the ammonium carbamate compound or ammonium carbonate compound represented by the formula 3, 4 or 5 below:

$$Ag_nX \quad (2)$$

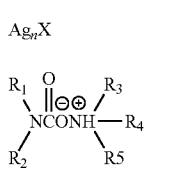
(3)

(4)

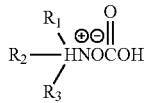
(5)

wherein, in the formula 2, n is an integer from 1 to 4, X is oxygen, sulfur, halogen, cyano, cyanate, carbonate, nitrate, nitrite, sulfate, phosphate, thiocyanate, chlorate, perchlorate, tetrafluoroborate, acetylacetonate or carboxylate (For example, the silver compound may be silver oxide, thiocyanate, silver sulfide, silver chloride, silver cyanide, silver cyanate, silver carbonate, silver nitrate, silver nitrite, silver sulfate, silver phosphate, silver perchlorate, silver tetrafluoroborate, silver acetylacetonate, silver acetate, silver lactate, silver oxalate or a derivative thereof. Silver oxide or silver carbonate is preferred with regard to reactivity or post-treatment, although not limited to them.), and in the formulas 3 to 5, each of $R_1$, $R_2$, $R_3$, $R_4$, $R_5$ and $R_6$ is independently hydrogen, $C_1$-$C_{30}$ aliphatic or cycloaliphatic alkyl, aryl or aralkyl, substituted alkyl or aryl, where $R_1$ and $R_2$ and, independently, $R_4$ and $R_5$ may form an alkylene ring containing or not containing a hetero atom, a polymer compound or a derivative thereof (Although not limiting the present invention, it is preferred that each of $R_1$ and $R_4$ is $C_1$-$C_{14}$ aliphatic alkyl and each of $R_3$, $R_4$, $R_5$ and $R_6$ is hydrogen or $C_1$-$C_{14}$ aliphatic alkyl).

Specifically, in the formulas 3 to 5, each of $R_1$, $R_2$, $R_3$, $R_4$, $R_5$ and $R_6$ may be hydrogen, methyl, ethyl, propyl, isopropyl, butyl, isobutyl, amyl, hexyl, ethylhexyl, heptyl, octyl, isooctyl, nonyl, decyl, dodecyl, hexadecyl, octadecyl, docodecyl, cyclopropyl, cyclopentyl, cyclohexyl, allyl, hydroxy, methoxy, methoxyethyl, methoxypropyl, cyanoethyl, ethoxy, butoxy, hexyloxy, methoxyethoxyethyl, methoxyethoxyethyl, hexamethyleneimine, morpholine, piperidine, piperazine, ethylenediamine, propylenediamine, hexamethylenediamine, triethylenediamine, pyrrole, imidazole, pyridine, carboxymethyl, trimethoxysilylpropyl, triethoxysilylpropyl, phenyl, methoxyphenyl, cyanophenyl, phenoxy, tolyl, benzyl, a derivative thereof, a polymer compound such as polyallylamine and polyethyleneimine or a derivative thereof, but not particularly limited to them.

The ammonium carbamate compound represented by the formula 3 may be, for example, ammonium carbamate, ethylammonium ethylcarbamate, isopropylammonium isopropylcarbamate, n-butylammonium n-butylcarbamate, isobutylammonium isobutylcarbamate, t-butylammonium t-butylcarbamate, 2-ethylhexylammonium 2-ethylhexylcarbamate, octadecylammonium octadecylcarbamate, 2-methoxyethylammonium 2-methoxyethylcarbamate, 2-cyanoethylammonium 2-cyanoethylcarbamate, dibutylammonium dibutylcarbamate, dioctadecylammonium dioctadecylcarbamate, methyldecylammonium methyldecylcarbamate, hexamethyleneiminium hexamethyleneiminecarbamate, morpholinium morpholinecarbamate, pyridinium ethylhexylcarbamate, triethylenediaminium isopropylbicarbamate, benzylammonium benzylcarbamate, triethoxysilylpropylammonium triethoxysilylpropylcarbamate, etc.

For the ammonium carbamate compound of the present invention, one substituted by primary amine is preferred to those substituted by secondary or tertiary amine in terms of reactivity and stability.

The ammonium carbonate compound represented by the formula 4 or formula 5 may be, for example, ammonium carbonate, ammonium bicarbonate, ethylammonium ethylcarbonate, isopropylammonium isopropylcarbonate, isopropylammonium bicarbonate, n-butylammonium n-butylcarbonate, isobutylammonium isobutylcarbonate, t-butylammonium t-butylcarbonate, t-butylammonium bicarbonate, 2-ethylhexylammonium 2-ethylhexylcarbonate, 2-ethylhexylammonium bicarbonate, 2-methoxyethylammonium 2-methoxyethylcarbonate, 2-methoxyethylammonium bicarbonate, 2-cyanoethylammonium 2-cyanoethylcarbonate, 2-cyanoethylammonium bicarbonate, octadecylammonium octadecylcarbonate, dibutylammonium dibutylcarbonate, dioctadecylammonium dioctadecylcarbonate, dioctadecylammonium bicarbonate, methyldecylammonium methyldecylcarbonate, hexamethyleneiminium hexamethyleneiminecarbonate, morpholinium morpholinecarbonate, benzylammonium benzylcarbonate, triethoxysilylpropylammonium triethoxysilylpropylcarbonate, pyridinium bicarbonate, triethylenediaminium isopropylcarbonate, triethylenediaminium bicarbonate or a derivative thereof.

The ammonium carbamate compound, the ammonium carbonate compound and preparation method thereof are not particularly limited. For example, J. Am. Chem. Soc., 70, p. 3865 (1948), J. Am. Chem. Soc., 73, p. 1829 (1951), J. Prakt. Chem., 9, p. 217 (1959), J. Am. Chem. Soc., 123, p. 10393 (2001), Langmuir, 18, 7124 (2002) and U.S. Pat. No. 4,542,214 (Sep. 17, 1985) disclose that the compounds can be prepared from primary amine, secondary amine, tertiary amine or a mixture thereof and carbon dioxide. According to the disclosure, an ammonium carbonate compound is obtained if 0.5 mole of carbon dioxide is used per 1 mole of amine and an ammonium bicarbonate compound is obtained if more than 1 mole of carbon dioxide is used per 1 mole of amine. The preparation may be performed under normal pressure or applied pressure with or without a solvent. When a solvent is used, an alcohol such as methanol, ethanol, isopropanol and butanol, a glycol such as ethylene glycol and glycerine, an acetate such as ethyl acetate, butyl acetate and carbitol acetate, an ether such as diethyl ether, tetrahydrofuran and dioxane, a ketone such as methyl ethyl ketone and acetone, a hydrocarbon solvent such as hexane and heptane, an aromatic solvent such as benzene and toluene, a halogen-substituted solvent such as chloroform, methylene chloride and carbon tetrachloride, etc. may be used. Carbon dioxide may be bubbled in the gas phase or solid dry ice may be used. The reaction may be performed in the supercritical state. Any other known methods can be applied for the preparation of the ammonium carbamate derivative and the ammonium carbonate derivative, as long as the structure of the target compound is the same. That is, preparation solvent, reaction temperature, concentration, catalyst, etc. are not particularly limited. And, the preparation yield is irrelevant of the preparation method.

Such prepared ammonium carbamate compound or ammonium carbonate compound is reacted with the silver compound to obtain the organic silver complex. For example, at least one silver compound represented by the formula 2 may be reacted with at least one ammonium carbamate derivative or ammonium carbonate derivative represented by the formulas 3 to 5 under nitrogen atmosphere at normal pressure or applied pressure with or without a solvent. When a solvent is used, an alcohol such as methanol, ethanol, isopropanol and butanol, a glycol such as ethylene glycol and glycerine, an acetate such as ethyl acetate, butyl acetate and carbitol acetate, an ether such as diethyl ether, tetrahydrofuran and dioxane, a ketone such as methyl ethyl ketone and acetone, a hydrocarbon solvent such as hexane and heptane, an aromatic solvent such as benzene and toluene, halogen-substituted solvent such as chloroform, methylene chloride and carbon tetrachloride, etc. may be used. However, the solvent used in the preparation of the organic silver complex of the present invention needs not be particularly limited. That is, any other solvent may be used as long as the structure of the target compound is the same.

The silver complex of the present invention has the structure represented by the following formula 1:

$$Ag[A]_m \quad (1)$$

where A is the compound represented by the formula 3, 4 or 5 and $0.7 \le m \le 2.5$.

Figure 2:
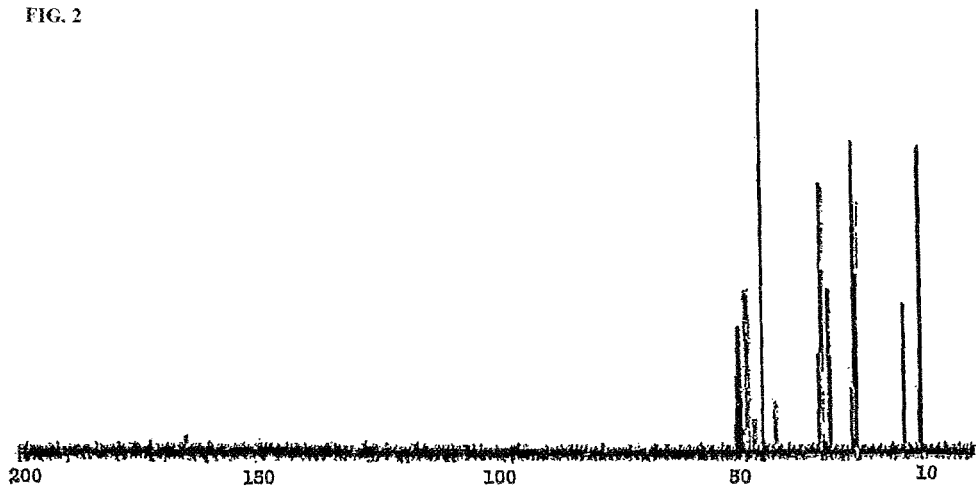
FIG. 2 is the $^{13}$C NMR spectrum of the silver complex of Example 1.
Figure 3:
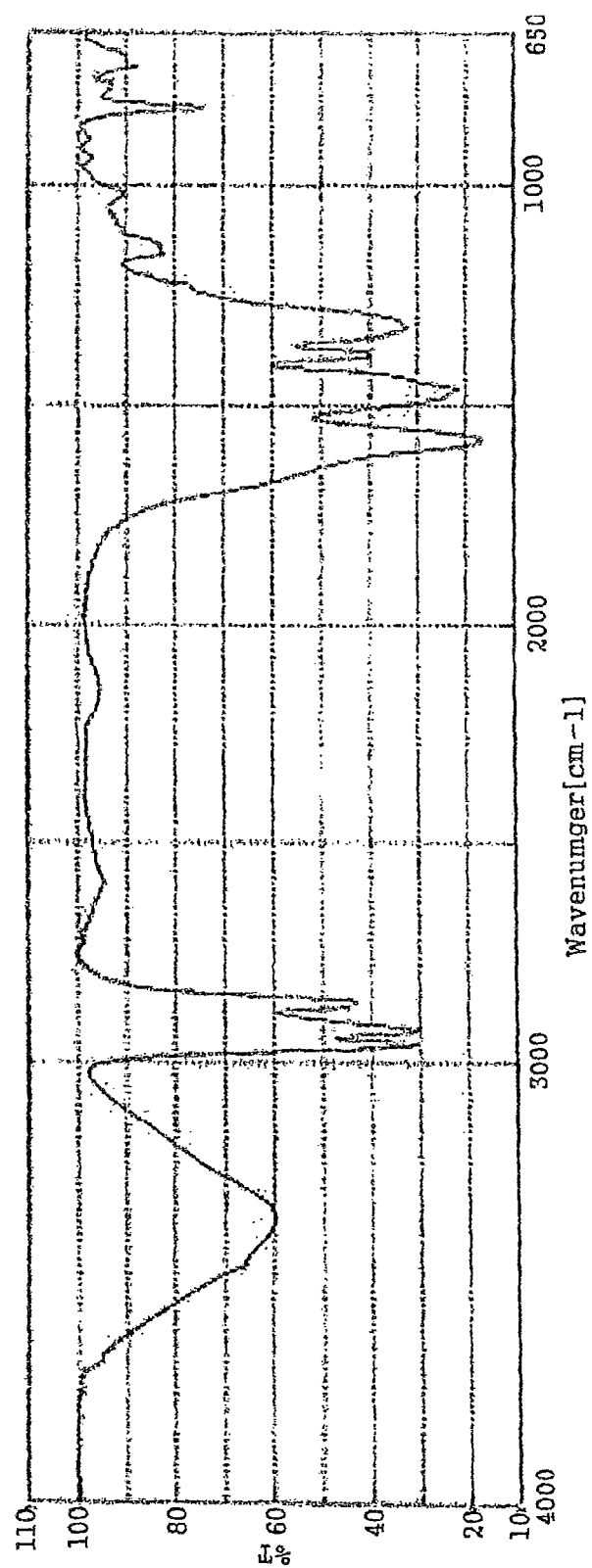
FIG. 3 is the IR spectrum of the silver complex of Example 1.
Figure 4:
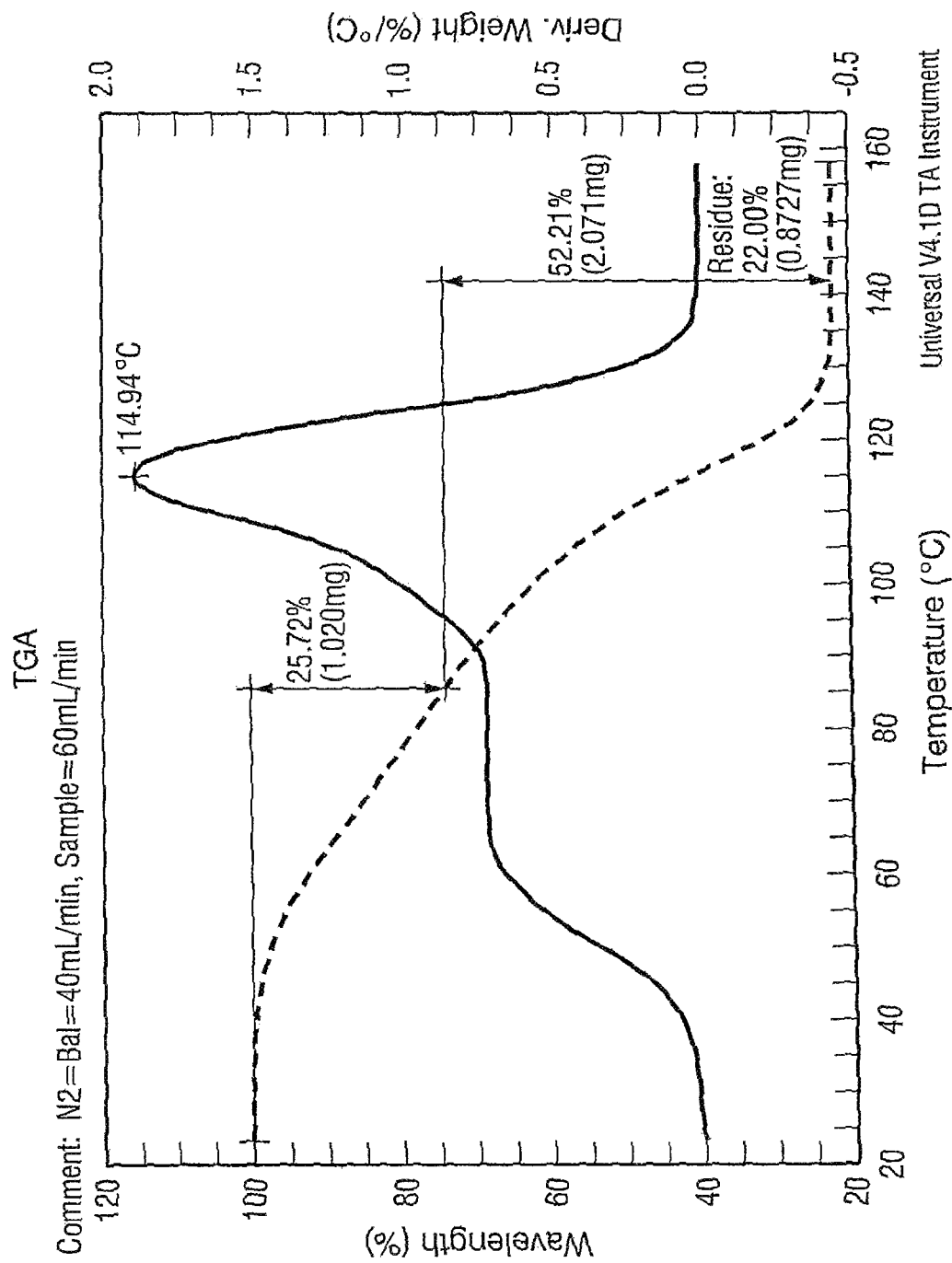
FIG. 4 is the TGA thermogram of the silver complex of Example 1.
Figure 5:
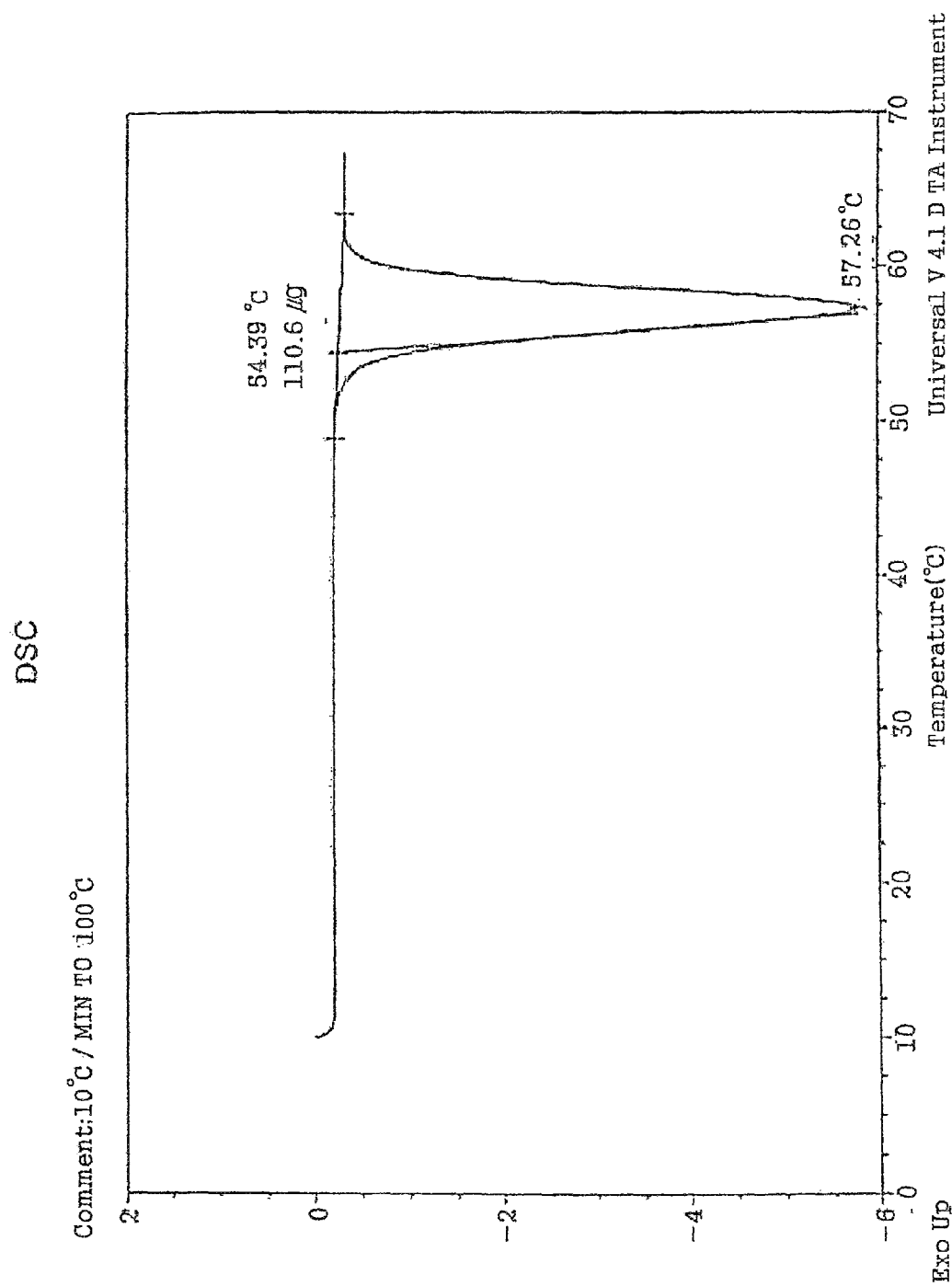
FIG. 5 is the DSC thermogram of the silver complex of Example 1.
Figure 6:
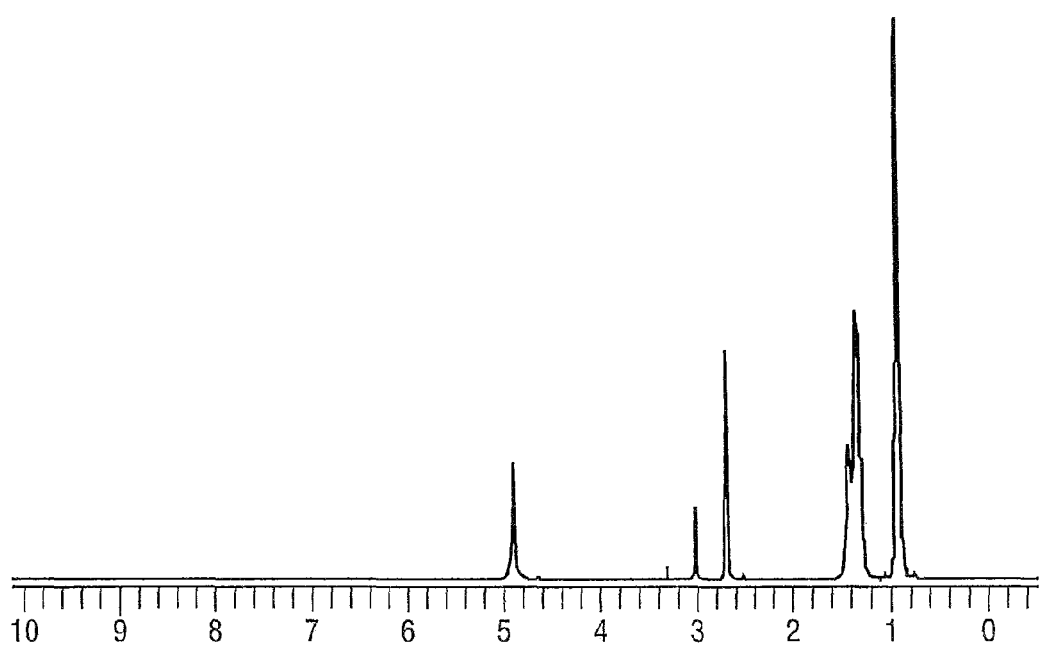
FIG. 6 is the $^1$H NMR spectrum of the silver complex of Example 23.
Figure 7:
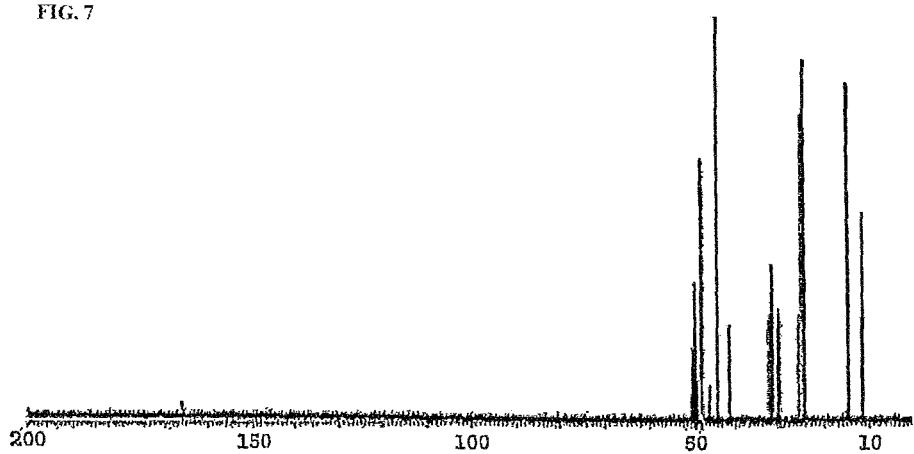
FIG. 7 is the $^{13}$C NMR spectrum of the silver complex of Example 23.
Figure 8:
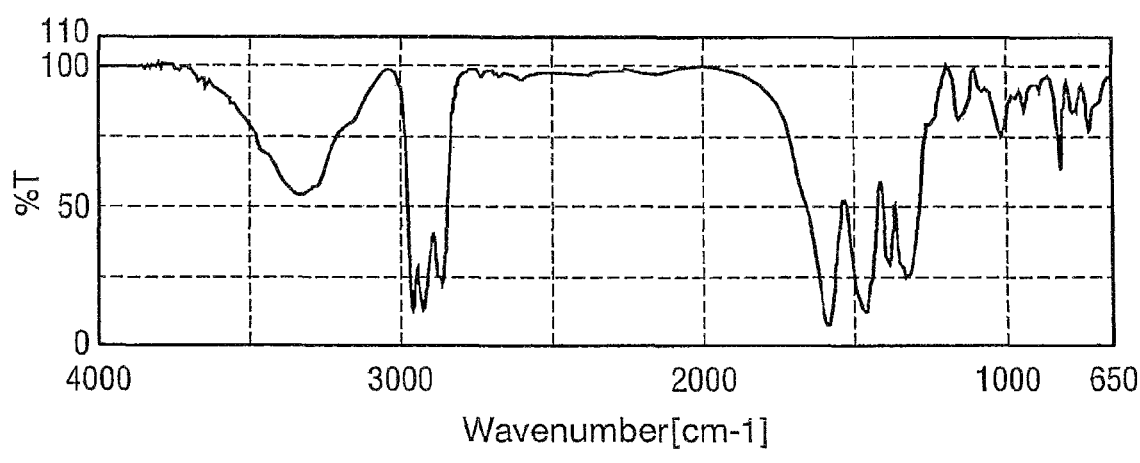
FIG. 8 is the IR spectrum of the silver complex of Example 23.
Figure 9:
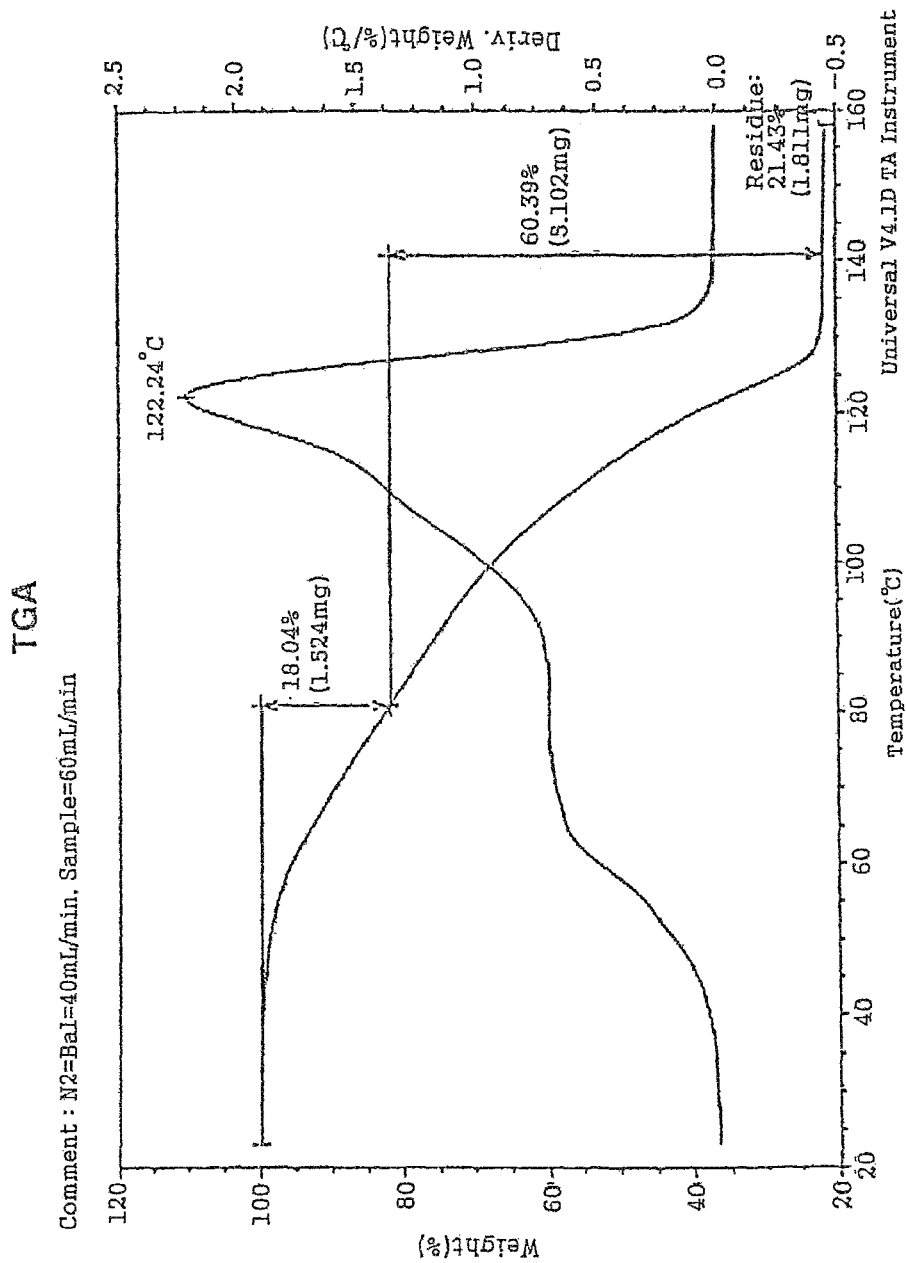
FIG. 9 is the TGA thermogram of the silver complex of Example 23.
Figure 10:
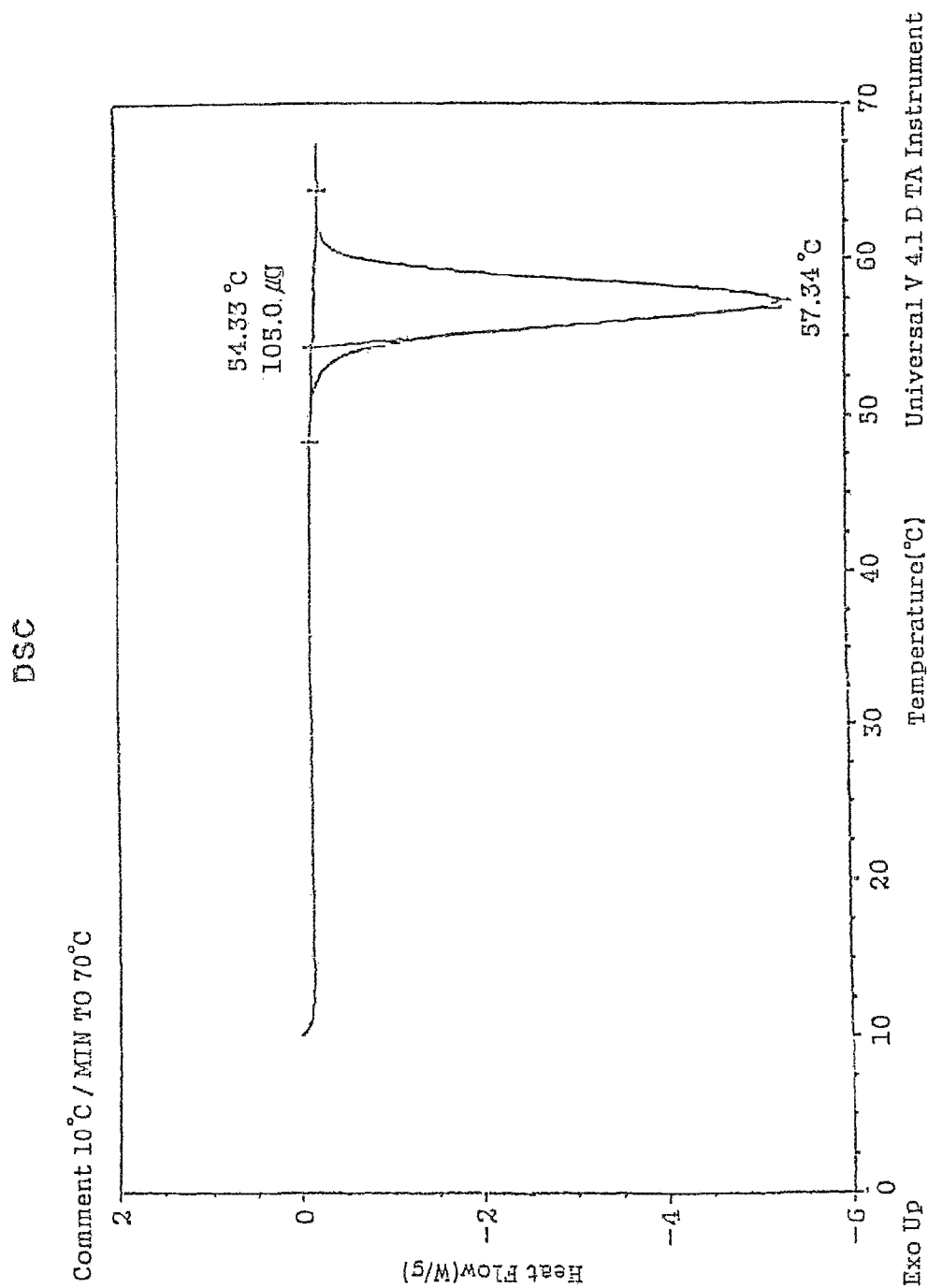
FIG. 10 is the DSC thermogram of the silver complex of Example 23.
Figure 11:
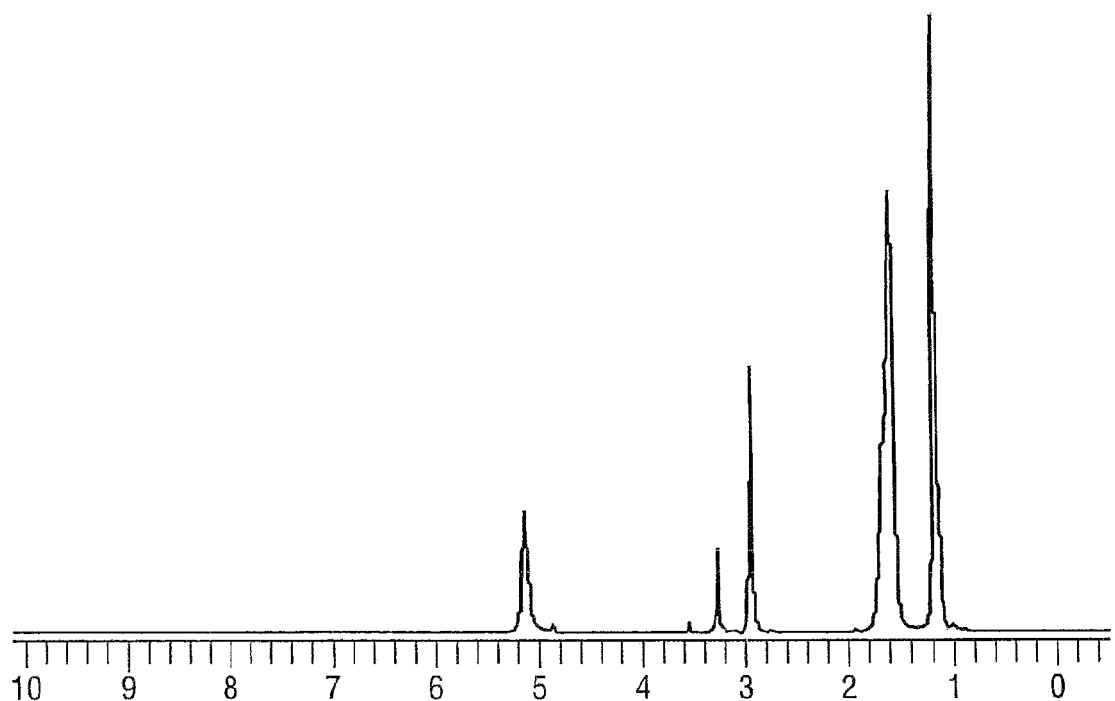
FIG. 11 is the ¹H NMR spectrum of the silver complex of Example 24.
Figure 12:
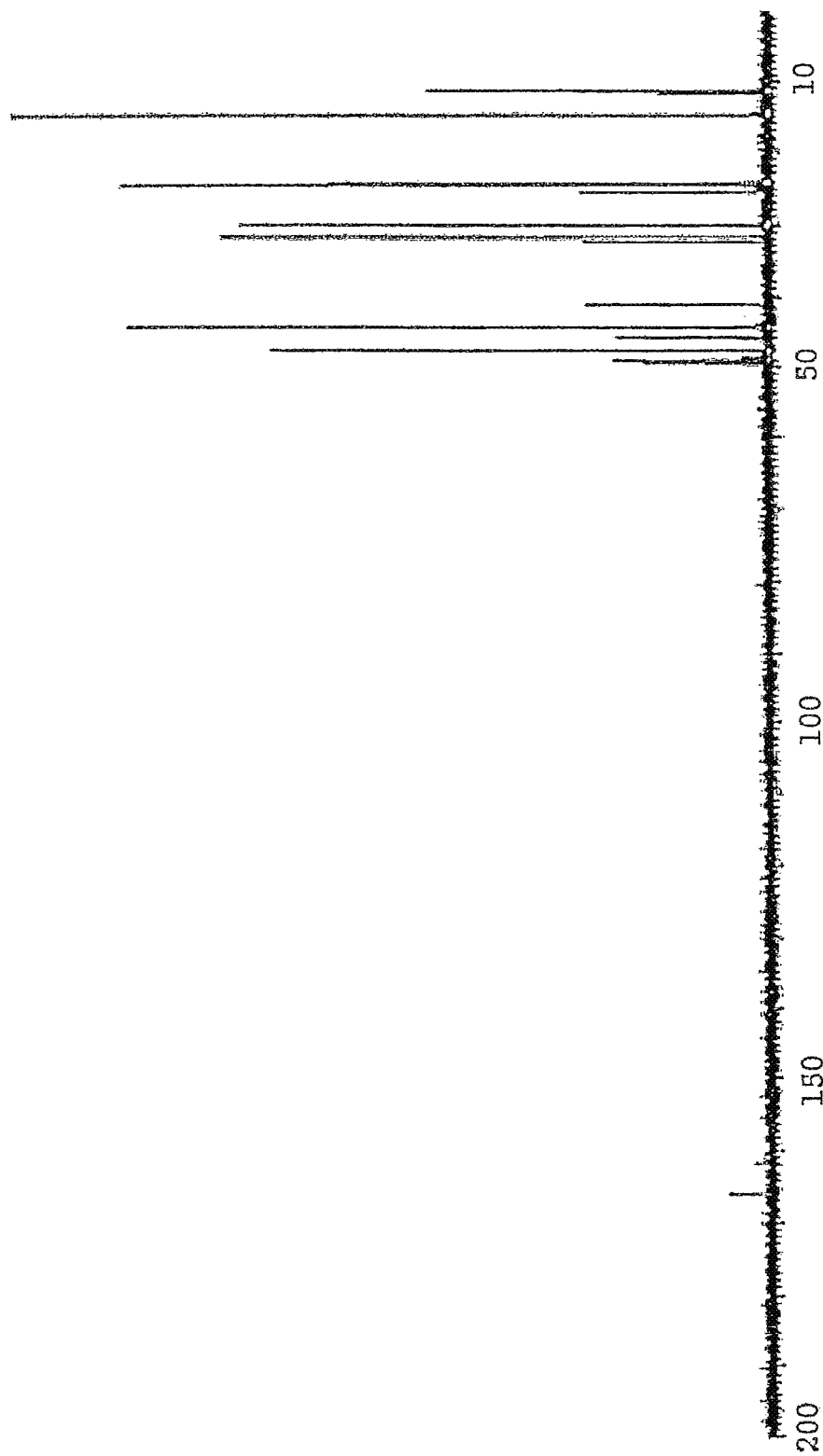
FIG. 12 is the ¹³C NMR spectrum of the silver complex of Example 24.
Figure 13:
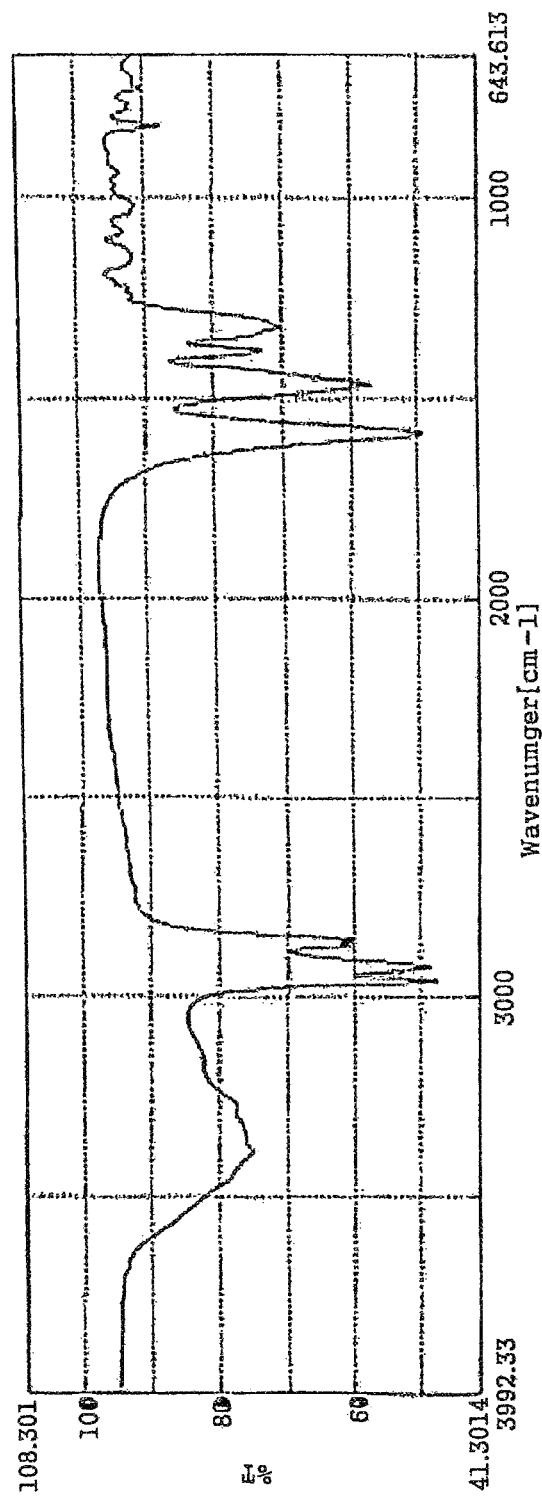
FIG. 13 is the IR spectrum of the silver complex of Example 24.
Figure 14:
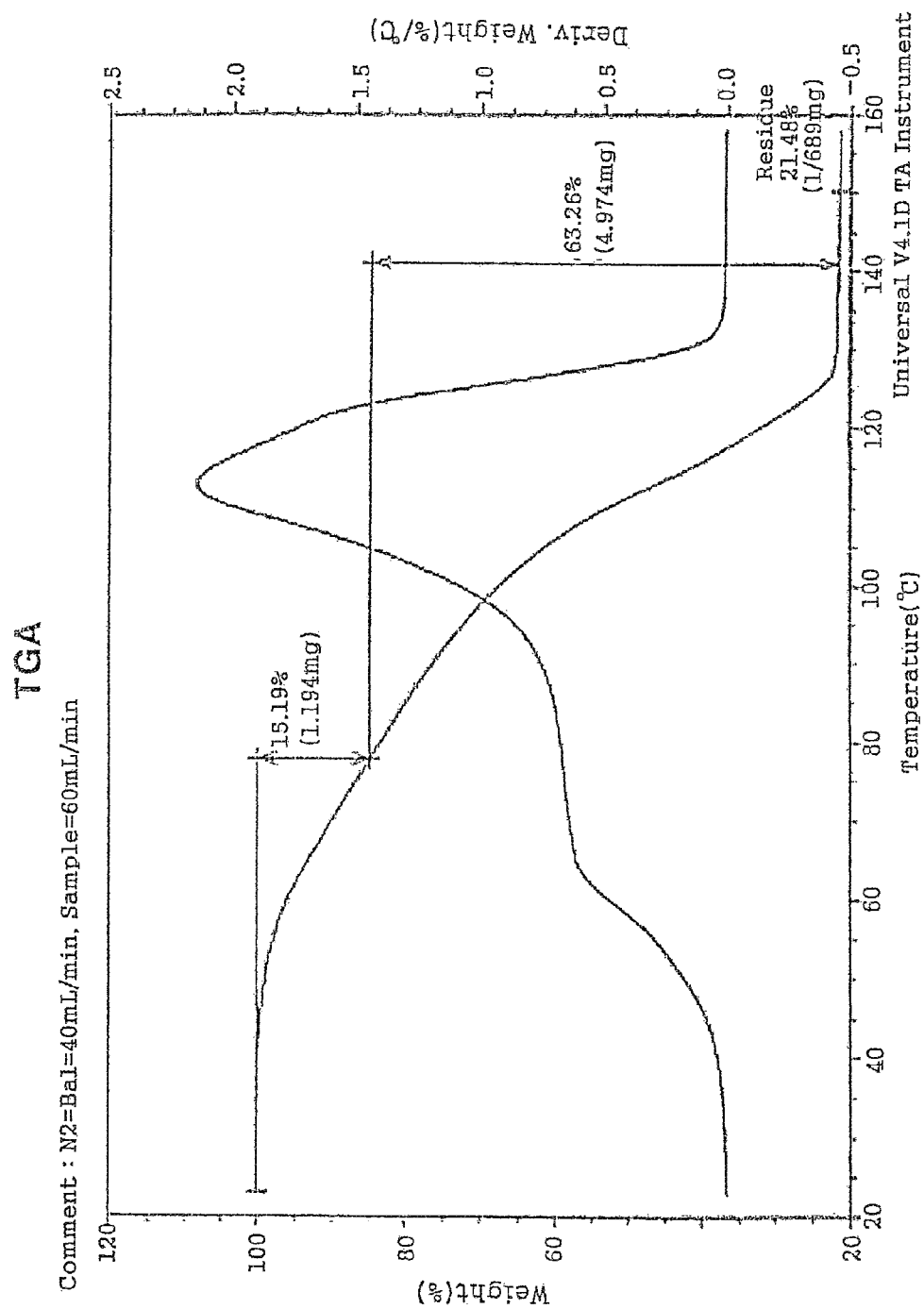
FIG. 14 is the TGA thermogram of the silver complex of Example 24.
Figure 15:
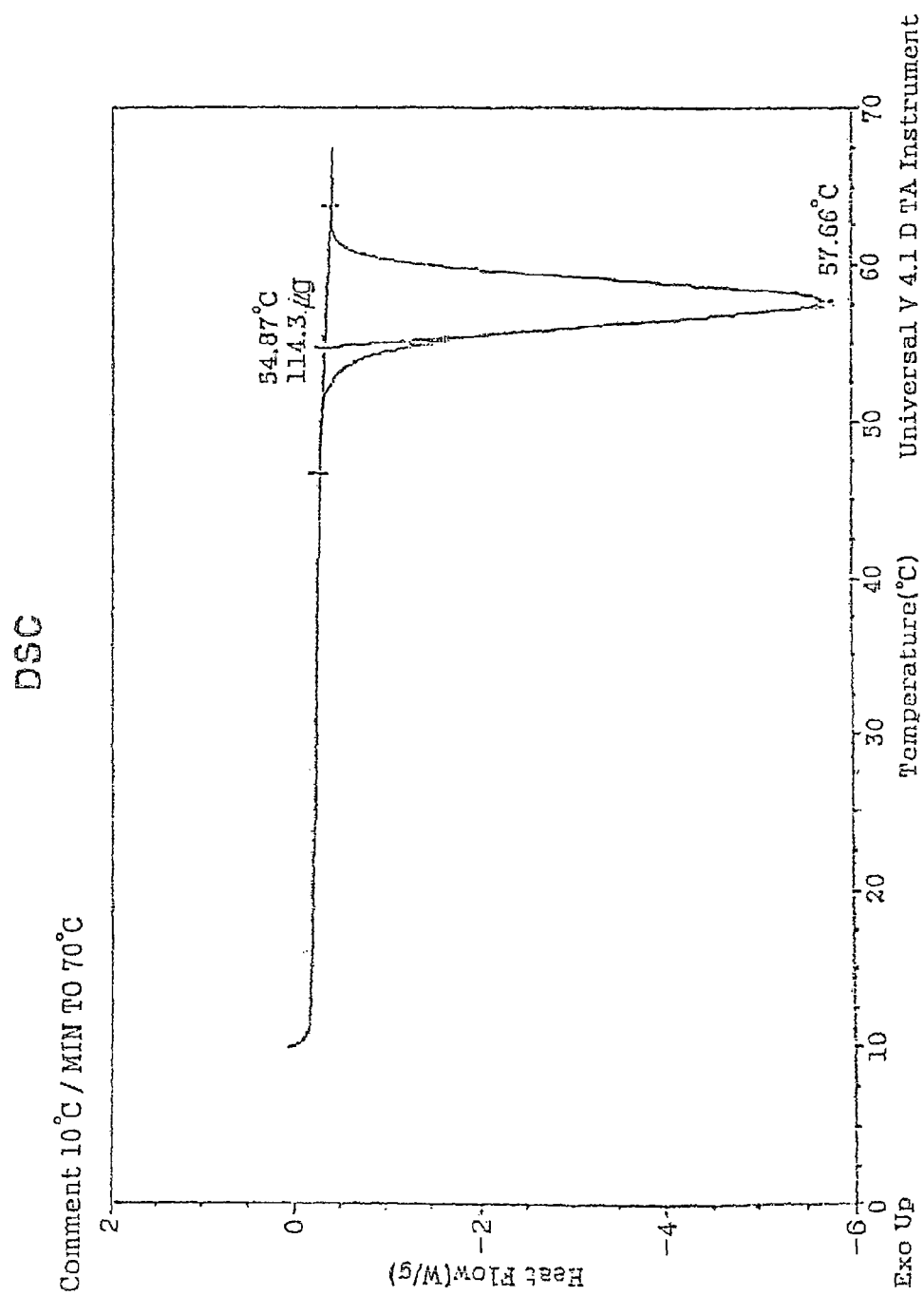
FIG. 15 is the DSC thermogram of the silver complex of Example 24.

The silver complexes of the present invention are isolated as white solid. When decomposed by heating, the resultant compounds contain conductive, non-valent silver, not in the oxidized state. The IR spectrums (FIG. 3, FIG. 8 and FIG. 13) of the silver complexes show C=O absorption bands and confirms that carbon dioxide is not produced. The $^1$H NMR spectrums (FIG. 1, FIG. 6 and FIG. 11) and the $^{13}$C NMR spectrums (FIG. 2, FIG. 7 and FIG. 12) also confirm the functional groups of the ammonium carbamate compound or the ammonium carbonate compound.

The silver complexes of the present invention show specific melting points and decomposition patterns as seen in the TGA thermograms and the DSC thermograms (FIG. 4, FIG. 5, FIG. 9, FIG. 10, FIG. 14 and FIG. 15). When the melt silver complexes are cooled, stable solid silver complexes are obtained.

The organic silver complex of the present invention is highly soluble in a variety of solvents including ones used to prepare the organic silver complex, for example, an alcohol such as methanol, an ester such as ethyl acetate, an ether such as tetrahydrofuran, etc. Thus, the silver complex can be readily used in coating or printing and can be stably stored in the form of solution for over 3 months.

The organic silver complex solution may be prepared into thin film by coating on a substrate of glass, silicon wafer, polymer film like polyester and polyimide, paper, etc. or printed directly. The thin film formation may be performed by spin coating, roll coating, spray coating, dip coating, flow coating, etc. And, the printing may be performed by ink-jet printing, offset printing, screen printing, gravure printing, flexo printing, etc.

The prepared thin film may be oxidized, reduced or heat-treated or the organic silver complex may be treated with chemical vapor deposition (CVD), plasma vapor deposition, sputtering, electroplating, lithography, IR, electron beam or laser to obtain a metal or metal oxide pattern. The heat treatment may be performed under inert gas atmosphere, as usually, but also may be performed in air or using a mixture gas of hydrogen and air or other inert gas.

Hereinafter, the present invention is described in further detail through examples. However, the following examples are only for the understanding of the present invention and the present invention is not limited to or by them.

EXAMPLES

Example 1

Reaction of silver oxide with 2-ethylhexylammonium 2-ethylhexylcarbamate

In a 50 mL Schlenk flask equipped with a stirrer, 3.25 g (10.75 mmol) of 2-ethylhexylammonium 2-ethylhexylcarbamate (viscous liquid) was dissolved in 10 mL of methanol. 1.0 g (4.31 mmol) of silver oxide was added and reaction was performed at room temperature. The reaction solution was initially a black slurry but it turned transparent as complex was produced. After 2 hours of reaction, a colorless, transparent solution was obtained. The resultant solution was filtered with a 0.45 micron membrane filter to remove unreacted silver oxide. Then, the solvent was removed at vacuum to obtain white solid. The solid was recrystallized in ethyl acetate, dried and weighed to obtain 4.22 g of a silver complex (yield=99.4%). The silver complex had a melting point of 57-58° C. (DSC=57.26° C.) and a silver content of 22.0 wt % (TGA analysis).

$^1$H NMR (CD$_3$OD, ppm), 1.11-1.19 (m, —CH$_3$) 1.51-1.69 (m, —CH$_2$, —CH), 2.91-2.92, 3.23-3.25 (d, —NCH$_2$), 5.13 (s, —NH$_2$), $^{13}$C NMR (CD$_3$OD, ppm), 166.09, 47.60, 44.24, 31.76, 30.12, 24.77, 24.30, 14.64, 11.15

Example 2

Reaction of Silver Oxide with n-propylammonium n-propylcarbamate

In a 50 mL Schlenk flask equipped with a stirrer, 1.74 g (10.75 mmol) of n-propylammonium n-propylcarbamate (viscous liquid, melting point: 74-76° C.) was dissolved in 10 mL of methanol. 1.0 g (4.31 mmol) of silver oxide was added and reaction was performed at room temperature for 2 hours while stirring. A colorless, transparent complex solution was obtained as in Example 1. The resultant solution was filtered with a 0.45 micron membrane filter to remove and the solvent was removed at vacuum to obtain white solid. The solid was dried and weighed to obtain 2.42 g of a silver complex (yield=88.3%). Most of the silver complex was decomposed below 130° C. to leave metallic silver. The silver content was 38.4 wt % (TGA analysis). $^1$H NMR (CD$_3$OD, ppm), 0.98-1.02 (t, —CH$_3$) 1.59-1.65 (m, —CH$_2$), 2.76-2.80 (t, —NCH$_2$), $^{13}$C NMR (CD$_3$OD, ppm), 47.03, 27.84, 11.53

Example 3

Reaction of Silver Oxide with Isopropylammonium Isopropylcarbamate

In a 50 mL Schlenk flask equipped with a stirrer, 1.60 g (10.75 mmol) of isopropylammonium isopropylcarbamate (white solid, melting point: 78-80° C.) was dissolved in 10 mL of methanol. 1.0 g (4.31 mmol) of silver oxide was added and reaction was performed at room temperature. The reaction solution was initially a black slurry but it turned transparent as complex was produced. After 2 hours of reaction, a colorless, transparent solution was obtained. The resultant solution was filtered with a 0.45 micron membrane filter and the solvent was removed at vacuum to obtain white solid. The solid was dried and weighed to obtain 2.48 g of a silver complex (yield=95.5%). Most of the silver complex was decomposed below 130° C. to leave metallic silver. The silver content was 37.2 wt % (TGA analysis).

$^1$H NMR (CD$_3$OD, ppm), 1.13-1.22 (d, —CH$_3$), 3.22-3.31 (m, CH), $^{13}$C NMR (CD$_3$OD, ppm), 45.78, 26.06

Example 4

Reaction of Silver Oxide with n-butylammonium n-butylcarbamate

In a 50 mL Schlenk flask equipped with a stirrer, 2.04 g (10.75 mmol) of n-butylammonium n-butylcarbamate (white solid, melting point: 82-84° C.) was dissolved in 10 mL of methanol. 1.0 g (4.31 mmol) of silver oxide was added and reaction was performed at room temperature. The reaction solution was initially a black slurry but it turned transparent as complex was produced. After 2 hours of reaction, a colorless, transparent solution was obtained. The resultant solution was filtered with a 0.45 micron membrane filter and the solvent was removed at vacuum to obtain white solid. The solid was dried and weighed to obtain 2.79 g of a silver complex (yield=92.0%). Most of the silver complex was decomposed below 130° C. to leave metallic silver. The silver content was 33.2 wt % (TGA analysis).

$^1$H NMR (CD$_3$OD, ppm), 0.92-0.97 (t, —CH$_3$), 1.37-1.46 (m, —CH$_2$), 1.52-1.59 (m, —CH$_2$), 2.75-2.79 (t, —NCH$_2$), $^{13}$C NMR (CD$_3$OD, ppm), 161.46, 44.76, 36.94, 21.05, 14.38

Example 5

Reaction of Silver Oxide with Isobutylammonium Isobutylcarbamate

In a 50 mL Schlenk flask equipped with a stirrer, 2.04 g (10.75 mmol) of isobutylammonium isobutylcarbamate (white solid, melting point: 80-82° C.) was dissolved in 10 mL of methanol. 1.0 g (4.31 mmol) of silver oxide was added and reaction was performed at room temperature. The reaction solution was initially a black slurry but it turned transparent as complex was produced. After 2 hours of reaction, a colorless, transparent solution was obtained. The resultant solution was filtered with a 0.45 micron membrane filter and the solvent was removed at vacuum to obtain white solid. The solid was dried and weighed to obtain 2.87 g of a silver complex (yield=94.4%). Most of the silver complex was decomposed below 130° C. to leave metallic silver. The silver content was 32.4 wt % (TGA analysis).

$^1$H NMR (CD$_3$OD, ppm), 0.96-0.98 (d, —CH$_3$), 1.67-1.74 (m, —CH), 2.59-2.88 (dd, —CH$_2$), $^{13}$C NMR (CD$_3$OD, ppm), 161.48, 52.69, 33.16, 30.45, 20.42

Example 6

Reaction of Silver Oxide with t-butylammonium t-butylcarbamate

In a 50 mL Schlenk flask equipped with a stirrer, 2.04 g (10.75 mmol) of t-butylammonium t-butylcarbamate (white solid) was dissolved in 10 mL of methanol. 1.0 g (4.31 mmol) of silver oxide was added and reaction was performed at room temperature. The reaction solution was initially a black slurry but it turned transparent as complex was produced. After 2 hours of reaction, a colorless, transparent solution was obtained. The resultant solution was filtered with a 0.45 micron membrane filter and the solvent was removed at vacuum to obtain white solid. The solid was dried and weighed to obtain 2.94 g of a silver complex (yield=97.0%). Most of the silver complex was decomposed below 130° C. to leave metallic silver. The silver content was 31.4 wt % (TGA analysis).

$^1$H NMR (CD$_3$OD, ppm), 1.27 (s, —CH$_3$), $^{13}$C NMR (CD$_3$OD, ppm), 161.52, 50.94, 32.28

Example 7

Reaction of Silver Carbonate with 2-ethylhexylammonium 2-ethylhexylcarbamate

In a 50 mL Schlenk flask equipped with a stirrer, 3.27 g (10.80 mmol) of 2-ethylhexylammonium 2-ethylhexylcarbamate (viscous liquid) was dissolved in 10 mL of methanol and 1.0 g (3.60 mmol) of silver carbonate was added. The reaction solution was initially a yellow slurry but it turned transparent as reaction proceeded. After 5 hours of reaction, a yellow, transparent solution was obtained, which confirmed production of a complex. The resultant solution was filtered with a 0.45 micron membrane filter and the solvent was removed at vacuum to obtain white solid. The solid was dried and weighed to obtain 4.18 g of a silver complex (yield=97.89%). Most of the silver complex was decomposed below 130° C. to leave metallic silver. The silver content was 18.66 wt % (TGA analysis).

$^1$H NMR (CD$_3$OD, ppm), 1.11-1.19 (m, —CH$_3$) 1.51-1.69 (m, —CH$_2$, —CH—), 2.91-2.92, 3.23-3.25 (d, —NCH$_2$), 5.13 (t, —NH$_x$), $^{13}$C NMR (CD$_3$OD, ppm), 166.09, 47.60, 44.24, 31.76, 30.12, 24.77, 24.30, 14.64, 11.15

Example 8

Reaction of Silver Oxide with 2-methoxyethylammonium 2-methoxyethylcarbamate

In a 50 mL Schlenk flask equipped with a stirrer, 2.17 g (11.18 mmol) of 2-methoxyethylammonium 2-methoxyethylcarbamate (white solid, melting point: 41-42° C.) was dissolved in 10 mL of methanol. 1.0 g (4.31 mmol) of silver oxide was added and reaction was performed at room temperature. The reaction solution was initially a black slurry but it turned transparent as complex was produced.

After 2 hours of reaction, a yellow, transparent solution was obtained. The resultant solution was filtered with a 0.45 micron membrane filter and the solvent was removed at vacuum to obtain brown, viscous liquid. The liquid was dried and weighed to obtain 2.58 g of a silver complex (yield=81.4%). Most of the silver complex was decomposed below 130° C. to leave metallic silver. The silver content was 35.9 wt % (TGA analysis). $^1$H NMR (CD$_3$OD, ppm), 2.93-2.96 (t, —NCH$_2$), 3.39 (s, —OCH$_3$), 3.48-3.50 (t, OCH$_2$), $^{13}$C NMR (CD$_3$OD, ppm), 161.48, 74.11, 59.35, 44.34

Example 9

Reaction of Silver Oxide with 2-hydroxyethylammonium 2-hydroxyethylcarbamate

In a 50 mL Schlenk flask equipped with a stirrer, 1.78 g (12.90 mmol) of 2-hydroxyethylammonium 2-hydroxyethylcarbamate was dissolved in 10 mL of methanol. 1.0 g (4.31 mmol) of silver oxide was added and reaction was performed at room temperature. The reaction solution was initially a black slurry but it turned transparent as complex was produced. After 2 hours of reaction, a yellow, transparent solution was obtained. The resultant solution was filtered with a 0.45 micron membrane filter and the solvent was removed at vacuum to obtain brown, viscous liquid. The liquid was dried and weighed to obtain 2.50 g of a silver complex (yield=90.1%). Most of the silver complex was decomposed below 130° C. to leave metallic silver. The silver content was 37.1 wt % (TGA analysis).
$^1$H NMR (CD$_3$OD, ppm), 2.82-2.85 (t, —NCH$_2$), 3.61-3.64 (t, OCH$_2$), $^{13}$C NMR (CD$_3$OD, ppm), 166.16, 63.70, 46.12

Example 10

Reaction of Silver Oxide with 2-cyanoethylammonium 2-cyanoethylcarbamate

In a 50 mL Schlenk flask equipped with a stirrer, 2.40 g (12.90 mmol) of 2-cyanoethylammonium 2-cyanoethylcarbamate (white solid, melting point: 70-72° C.) was dissolved in 10 mL of methanol. 1.0 g (4.31 mmol) of silver oxide was added and reaction was performed at room temperature. The reaction solution was initially a black slurry but it turned transparent as complex was produced. After 2 hours of reaction, a colorless, transparent solution was obtained. The resultant solution was filtered with a 0.45 micron membrane filter and the solvent was removed at vacuum to obtain white solid. The solid was dried and weighed to obtain 3.06 g of a silver complex (yield=90.0%). About 60% of the silver complex was decomposed below 150° C. to leave metallic silver and unreacted organic materials. Most of the silver complex was decomposed below 250° C. to leave metallic silver. The silver content was 28.7 wt % (TGA analysis).

Example 11

Reaction of Silver Oxide with Morpholinium Morpholinecarbamate

In a 50 mL Schlenk flask equipped with a stirrer, 2.81 g (12.90 mmol) of morpholinium morpholinecarbamate was dissolved in 10 mL of methanol. 1.0 g (4.31 mmol) of silver oxide was added and reaction was performed at room temperature. The reaction solution was initially a black slurry but it turned transparent as complex was produced. After 2 hours of reaction, a yellow, transparent solution was obtained. The resultant solution was filtered with a 0.45 micron membrane filter and the solvent was removed at vacuum to obtain gray solid. The solid was dried and weighed to obtain 3.29 g of a silver complex (yield=86.4%). Most of the silver complex was decomposed below 130° C. to leave metallic silver. The silver content was 28.3 wt % (TGA analysis).

Example 12

Reaction of Silver Oxide with Hexamethyleneiminium Hexamethyleneiminecarbamate

In a 50 mL Schlenk flask equipped with a stirrer, 3.13 g (12.90 mmol) of hexamethyleneiminium hexamethyleneiminecarbamate was dissolved in 10 mL of methanol. 1.0 g (4.31 mmol) of silver oxide was added and reaction was performed at room temperature. The reaction solution was initially a black slurry but it turned transparent as complex was produced. After 2 hours of reaction, a yellow, transparent solution was obtained. The resultant solution was filtered with a 0.45 micron membrane filter and the solvent was removed at vacuum to obtain brown liquid. The liquid was dried and weighed to obtain 3.29 g of a silver complex (yield=86.8%). Most of the silver complex was decomposed below 130° C. to leave metallic silver. The silver content was 25.9 wt % (TGA analysis).

Example 13

Reaction of Silver Oxide with Ammonium Carbamate

In a 250 mL Schlenk flask equipped with a stirrer, 6.71 g (86 mmol) of ammonium carbamate and 15 g of isopropylamine (0.25 mol) were dissolved in 50 mL of methanol. 10.0 g (43.1 mmol) of silver oxide was added and reaction was performed at room temperature. The reaction solution was initially a black slurry but it turned transparent as complex was produced. After 3 hours of reaction, a colorless, transparent solution was obtained. The resultant solution was filtered with a 0.45 micron membrane filter and the solvent was removed at vacuum to obtain white solid. The solid was dried and weighed to obtain 26.90 g of a silver complex (yield=84.9%). Most of the silver complex was decomposed below 130° C. to leave metallic silver. The silver content was 42.0 wt % (TGA analysis).

Example 14

Reaction of Silver Carbonate with Ammonium Carbamate

In a 250 mL Schlenk flask equipped with a stirrer, 3.36 g (43 mmol) of ammonium carbamate and 15 g of isopropylamine (0.25 mol) were dissolved in 50 mL of methanol. 11.88 g (43.1 mmol) of silver carbonate was added and reaction was performed at room temperature. The reaction solution was initially a yellow slurry but it turned transparent as complex was produced. After 6 hours of reaction, a colorless, transparent solution was obtained. The resultant solution was filtered with a 0.45 micron membrane filter and the solvent was removed at vacuum to obtain white solid. The solid was dried and weighed to obtain 25.60 g of a silver complex (yield=84.5%). Most of the silver complex was decomposed below 130° C. to leave metallic silver. The silver content was 45.8 wt % (TGA analysis).

Example 15

Reaction of Silver Oxide with 2-ethylhexylammonium 2-ethylhexylcarbamate

In a 50 mL Schlenk flask equipped with a stirrer, 3.25 g (10.75 mmol) of 2-ethylhexylammonium 2-ethylhexylcarbamate (viscous liquid) was dissolved in 10 mL of tetrahydrofuran (THF). 1.0 g (4.31 mmol) of silver oxide was added and reaction was performed at room temperature. The reaction solution was initially a black slurry but it turned transparent as complex was produced. After 2 hours of reaction, a yellow, transparent solution was obtained. The resultant solution was filtered with a 0.45 micron membrane filter and the solvent was removed at vacuum to obtain white solid. The solid was dried and weighed to obtain 3.58 g of a silver complex (yield=88.23%). Most of the silver complex was decomposed below 130° C. to leave metallic silver. The silver content was 25.97 wt % (TGA analysis).

Example 16

Reaction of Silver Oxide with 2-ethylhexylammonium 2-ethylhexylcarbamate

In a 50 mL Schlenk flask equipped with a stirrer, 3.25 g (10.75 mmol) of 2-ethylhexylammonium 2-ethylhexylcarbamate (viscous liquid) was dissolved in 10 mL of ethyl acetate. 1.0 g (4.31 mmol) of silver oxide was added and reaction was performed at room temperature. The reaction solution was initially a black slurry but it turned transparent as complex was produced. After 2 hours of reaction, a colorless, transparent solution was obtained. The resultant solution was filtered with a 0.45 micron membrane filter and the solvent was removed at vacuum to obtain white solid. The solid was dried and weighed to obtain 3.53 g of a silver complex (yield=83.17%). Most of the silver complex was decomposed below 130° C. to leave metallic silver. The silver content was 26.34 wt % (TGA analysis).

Example 17

Reaction of Silver Oxide with 2-ethylhexylammonium 2-ethylhexylcarbamate

To a 50 mL Schlenk flask equipped with a stirrer was added 3.90 g (12.90 mmol) of 2-ethylhexylammonium 2-ethylhexylcarbamate (viscous liquid). 1.0 g (4.31 mmol) of silver oxide was added and reaction was performed at room temperature. The reaction solution was initially a black slurry but it turned transparent as complex was produced. After 2 hours of reaction, a yellow, transparent solution was obtained. The resultant solution was filtered with a 0.45 micron membrane filter and kept at vacuum to obtain white solid. The solid was dried and weighed to obtain 3.58 g of a silver complex (yield=88.23%). Most of the silver complex was decomposed below 130° C. to leave metallic silver. The silver content was 25.97 wt % (TGA analysis).

Example 18

Reaction of Silver Oxide with aminoethylammonium aminoethylcarbamate

In a 50 mL Schlenk flask equipped with a stirrer, 1.763 g (10.75 mmol) of aminoethylammonium aminoethylcarbamate (white solid) was dissolved in 10 mL of methanol. 1.0 g (4.31 mmol) of silver oxide was added and reaction was performed at room temperature. The reaction solution was initially a black slurry but it turned transparent as complex was produced. After 2 hours of reaction, a colorless, transparent solution was obtained. The resultant solution was filtered with a 0.45 micron membrane filter and the solvent was removed at vacuum to obtain black, viscous liquid. The liquid was dried and weighed to obtain 2.21 g of a silver complex (yield=79.99%). Most of the silver complex was decomposed below 130° C. to leave metallic silver. The silver content was 42.12 wt % (TGA analysis).

Example 19

Reaction of Silver Oxide with 2-ethylhexylammonium 2-ethylhexylcarbamate and aminoethylammonium aminoethylcarbamate In a 50 mL Schlenk flask equipped with a stirrer, 3.07 g (10.80 mmol) of a 6:1 (molar ratio) mixture of 2-ethylhexylammonium 2-ethylhexylcarbamate and aminoethylammonium aminoethylcarbamate was dissolved in 10 mL of methanol. 1.0 g (4.31 mmol) of silver oxide was added and reaction was performed at room temperature. The reaction solution was initially a black slurry but it turned transparent as complex was produced. After 2 hours of reaction, a colorless, transparent solution was obtained. The resultant solution was filtered with a 0.45 micron membrane filter and the solvent was removed at vacuum to obtain orange, viscous liquid. The liquid was dried and weighed to obtain 3.85 g of a silver complex (yield=94.59%). Most of the silver complex was decomposed below 130° C. to leave metallic silver. The silver content was 24.20 wt % (TGA analysis).

Example 20

Reaction of Silver Sulfate with 2-ethylhexylammonium 2-ethylhexylcarbamate

In a 50 mL Schlenk flask equipped with a stirrer, 2.42 g (8.00 mmol) of 2-ethylhexylammonium 2-ethylhexylcarbamate (viscous liquid) was dissolved in 10 mL of methanol. 1.0 g (3.2 mmol) of silver sulfate was added and reaction was performed at room temperature. The reaction solution was initially a white slurry but it turned transparent as complex was produced. After 2 hours, a completely transparent solution was obtained. The resultant solution was filtered with a 0.45 micron membrane filter and the solvent was removed at vacuum to obtain white solid. The solid was recrystallized in ethyl acetate, dried and weighed to obtain 3.15 g of a silver complex (yield=92.3%). Most of the silver complex was decomposed below 130° C. to leave metallic silver. The silver content was 21.35 wt % (TGA analysis).

Example 21

Reaction of Silver Nitrate with 2-ethylhexylammonium 2-ethylhexylcarbamate

In a 50 mL Schlenk flask equipped with a stirrer, 2.23 g (7.37 mmol) of 2-ethylhexylammonium 2-ethylhexylcarbamate (viscous liquid) was dissolved in 10 mL of methanol. 1.0 g (5.9 mmol) of silver nitrate was added and reaction was performed at room temperature. The reaction solution was initially a white slurry but it turned transparent as complex was produced. After 2 hours, a completely transparent solution was obtained. The resultant solution was filtered with a 0.45 micron membrane filter and the solvent was removed at vacuum to obtain white solid. The solid was recrystallized in ethyl acetate, dried and weighed to obtain 2.76 g of a silver complex (yield=85.6%). Most of the silver complex was decomposed below 130° C. to leave metallic silver. The silver content was 22.73 wt % (TGA analysis).

Example 22

Reaction of Silver Cyanide with 2-ethylhexylammonium 2-ethylhexylcarbamate

In a 50 mL Schlenk flask equipped with a stirrer, 2.83 g (9.37 mmol) of 2-ethylhexylammonium 2-ethylhexylcarbamate (viscous liquid) was dissolved in 10 mL of dimethylsulfoxide (DMSO). 1 g (7.5 mmol) of silver cyanide was added and reaction was performed at room temperature. The reaction solution was initially a white slurry but it turned transparent as complex was produced. After 2 hours, a completely transparent solution was obtained. The resultant solution was filtered with a 0.45 micron membrane filter and the solvent was removed at vacuum to obtain white solid. The solid was recrystallized in ethyl acetate, dried and weighed to obtain 3.15 g of a silver complex (yield=82.42%). Most of the silver complex was decomposed below 130° C. to leave metallic silver. The silver content was 25.43 wt % (TGA analysis).

Example 23

Reaction of Silver Oxide with 2-ethylhexylammonium 2-ethylhexylcarbonate

In a 50 mL Schlenk flask equipped with a stirrer, 3.72 g (11.61 mmol) of 2-ethylhexylammonium 2-ethylhexylcarbamate (viscous liquid) was dissolved in 10 mL of methanol. 1.0 g (4.31 mmol) of silver oxide was added and reaction was performed at room temperature. The reaction solution was initially a black slurry but it turned transparent as complex was produced. After 2 hours, a colorless, transparent solution was obtained. The resultant solution was filtered with a 0.45 micron membrane filter to remove unreacted silver oxide particles and the solvent was removed at vacuum to obtain white solid. The solid was dried and weighed to obtain 4.02 g of a silver complex (yield=85.2%). The silver complex had a melting point of 55-57° C. (DSC=57.34° C.) and a silver content of 21.43 wt % (TGA analysis). $^1$H NMR (CD$_3$OD, ppm), 0.87-0.99 (m, —CH$_3$) 1.31-1.47 (m, —CH$_2$, —CH—), 2.69-2.70, 3.01-3.02 (d, —NCH$_2$), 4.90 (s, —NH$_2$), $^{13}$C NMR (CD$_3$OD, ppm), 165.00, 47.70, 44.25, 31.73, 30.90, 24.73, 24.29, 14.68, 11.16

Example 24

Reaction of Silver Oxide with 2-ethylhexylammonium bicarbonate

In a 50 mL Schlenk flask equipped with a stirrer, 4.86 g (25.37 mmol) of 2-ethylhexylammonium bicarbonate (viscous liquid) was dissolved in 10 mL of methanol. 1.0 g (4.31 mmol) of silver oxide was added and reaction was performed at room temperature. The reaction solution was initially a black slurry but it turned transparent as complex was produced. After 2 hours, a colorless, transparent solution was obtained. The resultant solution was filtered with a 0.45 micron membrane filter and the solvent was removed at vacuum to obtain white solid. The solid was dried and weighed to obtain 4.33 g of a silver complex (yield=73.9%). The silver complex had a melting point of 56-57° C. (DSC=57.66° C.) and a silver content of 21.48 wt % (TGA analysis).
$^1$H NMR (CD$_3$OD, ppm), 0.93-1.08 (m, —CH$_3$) 1.31-1.64 (m, —CH$_2$, —CH—), 2.93-2.94, 3.25-3.26 (d, —NCH$_2$), 5.13 (s, —NH$_2$), $^{13}$C NMR (CD$_3$OD, ppm), 165.56, 47.73, 44.23, 31.713, 30.08, 24.72, 24.28, 14.69, 11.17

Example 25

Reaction of Silver Oxide with isopropylammonium isopropylcarbonate

In a 50 mL Schlenk flask equipped with a stirrer, 2.01 g (11.18 mmol) of isopropylammonium isopropylcarbonate was dissolved in 10 mL of methanol and 1.0 g (4.31 mmol) of silver oxide was added. The reaction solution was initially a black slurry but it turned transparent as complex was produced. After 2 hours, a colorless, transparent solution was obtained. The resultant solution was filtered with a 0.45 micron membrane filter and the solvent was removed at vacuum to obtain white solid. The solid was dried and weighed to obtain 2.41 g of a silver complex (yield=80.2%). Most of the silver complex was decomposed below 130° C. and the silver content was 38.6 wt % (TGA analysis).

Example 26

Reaction of Silver Carbonate with Isopropylammonium Isopropylcarbonate

In a 50 mL Schlenk flask equipped with a stirrer, 2.07 g (11.52 mmol) of isopropylammonium isopropylcarbonate was dissolved in 10 mL of methanol and 1.0 g (3.60 mmol) of silver carbonate was added. The reaction solution was initially a yellow slurry but it turned transparent as complex was produced. After 6 hours, a colorless, transparent solution was obtained. The resultant solution was filtered with a 0.45 micron membrane filter and the solvent was removed at vacuum to obtain white solid. The solid was dried and weighed to obtain 2.42 g of a silver complex (yield=78.8%). Most of the silver complex was decomposed below 130° C. and the silver content was 32.23 wt % (TGA analysis).

Example 27

Reaction of Silver Carbonate with 2-ethylhexylammonium 2-ethylhexylcarbonate

In a 50 mL Schlenk flask equipped with a stirrer, 3.46 g (14.4 mmol) of 2-ethylhexylammonium 2-ethylhexylcarbonate (viscous liquid) was dissolved in 10 mL of methanol and 1.0 g (3.60 mmol) of silver carbonate was added. The reaction solution was initially a yellow slurry but it turned transparent as complex was produced. After 6 hours, a yellow, transparent solution was obtained. The resultant solution was filtered with a 0.45 micron membrane filter and the solvent was removed at vacuum to obtain white solid. The solid was dried and weighed to obtain 4.15 g of a silver complex (yield=93.04%). Most of the silver complex was decomposed below 130° C. and the silver content was 18.79 wt % (TGA analysis).

Example 28

Reaction of Silver Oxide with Isopropylammonium Bicarbonate

In a 50 mL Schlenk flask equipped with a stirrer, 2.97 g (24.51 mmol) of isopropylammonium bicarbonate (melting point: 53-54° C.) was dissolved in 10 mL of methanol and 1.0 g (4.31 mmol) of silver oxide was added. The reaction solution was initially a black slurry but it turned transparent as complex was produced. After 2 hours, a colorless, transparent solution was obtained. The resultant solution was filtered with a 0.45 micron membrane filter and the solvent was removed at vacuum to obtain white solid. The solid was dried and weighed to obtain 2.41 g of a silver complex (yield=60.7%). The silver complex had a melting point of 68-70° C. (DSC=70.49° C.). Most of the silver complex was decomposed below 130° C. to leave metallic silver and the silver content was 38.58 wt % (TGA analysis).

Example 29

Reaction of Silver Oxide with Ammonium Carbonate

In a 250 mL Schlenk flask equipped with a stirrer, 8.26 g (86 mmol) of ammonium carbonate and 15 g (0.25 mol) of isopropyl amine were dissolved in 50 mL of methanol and 10.0 g (43.1 mmol) of silver oxide was added. The reaction solution was initially a black slurry but it turned transparent as complex was produced. After 2 hours, a colorless, transparent solution was obtained. The resultant solution was filtered with a 0.45 micron membrane filter and the solvent was removed at vacuum to obtain white solid. The solid was dried and weighed to obtain 28.38 g of a silver complex (yield=85.5%). The silver complex had a melting point (DSC) of 63.38° C. Most of the silver complex was decomposed below 130° C. to leave metallic silver and the silver content was 46.3 wt % (TGA analysis).

Example 30

Reaction of Silver Carbonate with Ammonium Carbonate

In a 250 mL Schlenk flask equipped with a stirrer, 4.13 g (43 mmol) of ammonium carbonate and 15 g (0.25 mol) of isopropyl amine were dissolved in 50 mL of methanol and 11.88 g (43.1 mmol) of silver carbonate was added. The reaction solution was initially a yellow slurry but it turned transparent as complex was produced. After 6 hours, a colorless, transparent solution was obtained. The resultant solution was filtered with a 0.45 micron membrane filter and the solvent was removed at vacuum to obtain white solid. The solid was dried and weighed to obtain 26.71 g of a silver complex (yield=85.9%). Most of the silver complex was decomposed below 130° C. to leave metallic silver and the silver content was 47.8 wt % (TGA analysis).

Example 31

Reaction of Silver Oxide with Ammonium Bicarbonate

In a 250 mL Schlenk flask equipped with a stirrer, 6.8 g (86 mmol) of ammonium bicarbonate and 15 g (0.25 mol) of isopropyl amine were dissolved in 50 mL of methanol and 10.0 g (43.1 mmol) of silver oxide was added. The reaction solution was initially a black slurry but it turned transparent as complex was produced. After 3 hours, a colorless, transparent solution was obtained. The resultant solution was filtered with a 0.45 micron membrane filter and the solvent was removed at vacuum to obtain white solid. The solid was dried and weighed to obtain 26.55 g of a silver complex (yield=83.5%). Most of the silver complex was decomposed below 130° C. to leave metallic silver and the silver content was 46.8 wt % (TGA analysis).

Example 32

Reaction of Silver Carbonate with Ammonium Bicarbonate

In a 250 mL Schlenk flask equipped with a stirrer, 3.4 g (43 mmol) of ammonium bicarbonate and 15 g (0.25 mol) of isopropyl amine were dissolved in 50 mL of methanol and 11.88 g (43.1 mmol) of silver carbonate was added. The reaction solution was initially a yellow slurry but it turned transparent as complex was produced. After 6 hours, a colorless, transparent solution was obtained. The resultant solution was filtered with a 0.45 micron membrane filter and the solvent was removed at vacuum to obtain white solid. The solid was dried and weighed to obtain 26.20 g of a silver complex (yield=86.2%). Most of the silver complex was decomposed below 130° C. to leave metallic silver and the silver content was 48.2 wt % (TGA analysis).

Example 33

Reaction of Silver Oxide with 2-methoxyethylammonium Bicarbonate

In a 50 mL Schlenk flask equipped with a stirrer, 3.24 g (23.65 mmol) of 2-methoxyethylammonium bicarbonate (viscous liquid) was dissolved in 10 mL of methanol and 1.0 g (4.31 mmol) of silver oxide was added. The reaction solution was initially a black slurry but it turned transparent as complex was produced. After 2 hours, a yellow, transparent solution was obtained. The resultant solution was filtered with a 0.45 micron membrane filter and the solvent was removed at vacuum to obtain yellow, viscous liquid. The liquid was dried and weighed to obtain 3.01 g of a silver complex (yield=70.75%). Most of the silver complex was decomposed below 130° C. to leave metallic silver and the silver content was 31.08 wt % (TGA analysis).

Example 34

Reaction of Silver Carbonate with 2-methoxyethylammonium Bicarbonate

In a 50 mL Schlenk flask equipped with a stirrer, 3.78 g (27.54 mmol) of 2-methoxyethylammonium bicarbonate (viscous liquid) was dissolved in 10 mL of methanol and 1.0 g (3.60 mmol) of silver carbonate was added. The reaction solution was initially a yellow slurry but it turned transparent as complex was produced. After 2 hours, a yellow, transparent solution was obtained. The resultant solution was filtered with a 0.45 micron membrane filter and the solvent was removed at vacuum to obtain yellow, viscous liquid. The liquid was dried and weighed to obtain 3.28 g of a silver complex (yield=68.61%). Most of the silver complex was decomposed below 130° C. to leave metallic silver and the silver content was 23.78 wt % (TGA analysis).

Example 35

Reaction of Silver Oxide with Octylammonium Bicarbonate

In a 50 mL Schlenk flask equipped with a stirrer, 3.07 g (24.73 mmol) of octylammonium bicarbonate (white solid) was dissolved in 10 mL of methanol and 1.0 g (4.31 mmol) of silver oxide was added. The reaction solution was initially a black slurry but it turned transparent as complex was produced. After 2 hours, a colorless, transparent solution was obtained. The resultant solution was filtered with a 0.45 micron membrane filter and the solvent was removed at vacuum to obtain white solid. The solid was dried and weighed to obtain 3.81 g of a silver complex (yield=93.61%). Most of the silver complex was decomposed below 130° C. to leave metallic silver and the silver content was 24.40 wt % (TGA analysis).

Example 36

Reaction of Silver Oxide with Isobutylammonium Bicarbonate

In a 50 mL Schlenk flask equipped with a stirrer, 3.20 g (23.65 mmol) of isobutylammonium bicarbonate (white solid) was dissolved in 10 mL of methanol and 1.0 g (4.31 mmol) of silver oxide was added. The reaction solution was initially a black slurry but it turned transparent as complex was produced. After 2 hours, a colorless, transparent solution was obtained. The resultant solution was filtered with a 0.45 micron membrane filter and the solvent was removed at vacuum to obtain white solid. The solid was dried and weighed to obtain 3.21 g of a silver complex (yield=76.42%). Most of the silver complex was decomposed below 130° C. to leave metallic silver and the silver content was 28.97 wt % (TGA analysis).

Example 37

Reaction of Silver Oxide with n-Butylammonium Bicarbonate

In a 50 mL Schlenk flask equipped with a stirrer, 3.20 g (23.65 mmol) of viscous n-butylammonium bicarbonate was dissolved in 10 mL of methanol and 1.0 g (4.31 mmol) of silver oxide was added. The reaction solution was initially a black slurry but it turned transparent as complex was produced. After 6 hours, a colorless, transparent solution was obtained. The resultant solution was filtered with a 0.45 micron membrane filter and the solvent was removed at vacuum to obtain white solid. The solid was dried and weighed to obtain 3.49 g of a silver complex (yield=83.09%). Most of the silver complex was decomposed below 130° C. to leave metallic silver and the silver content was 26.72 wt % (TGA analysis).

Example 38

Reaction of Silver Oxide with Morpholinium Bicarbonate

In a 50 mL Schlenk flask equipped with a stirrer, 3.53 g (23.65 mmol) of morpholinium bicarbonate (white solid) was dissolved in 10 mL of methanol and 1.0 g (4.31 mmol) of silver oxide was added. The reaction solution was initially a black slurry but it turned transparent as complex was produced. After 2 hours, a yellow, transparent solution was obtained. The resultant solution was filtered with a 0.45 micron membrane filter and the solvent was removed at vacuum to obtain white solid. The solid was dried and weighed to obtain 3.16 g of a silver complex (yield=69.75%). Most of the silver complex was decomposed below 130° C. to leave metallic silver and the silver content was 29.49 wt % (TGA analysis).

Example 39

Reaction of Silver Oxide with 2-ethylhexylammonium 2-ethylhexylcarbonate

In a 50 mL Schlenk flask equipped with a stirrer, 4.13 g (12.90 mmol) of 2-ethylhexylammonium 2-ethylhexylcarbonate (viscous liquid) was dissolved in 10 mL of tetrahydrofuran (THF) and 1.0 g (4.31 mmol) of silver oxide was added. The reaction solution was initially a black slurry but it turned transparent as complex was produced. After 2 hours, a yellow, transparent solution was obtained. The resultant solution was filtered with a 0.45 micron membrane filter and the solvent was removed at vacuum to obtain white solid. The solid was dried and weighed to obtain 4.05 g of a silver complex (yield=78.84%). Most of the silver complex was decomposed below 130° C. to leave metallic silver and the silver content was 22.96 wt % (TGA analysis).

Example 40

Reaction of Silver Oxide with 2-ethylhexylammonium 2-ethylhexylcarbonate

In a 50 mL Schlenk flask equipped with a stirrer, 4.13 g (12.90 mmol) of 2-ethylhexylammonium 2-ethylhexylcarbonate (viscous liquid) was dissolved in 10 mL of ethyl acetate and 1.0 g (4.31 mmol) of silver oxide was added. The reaction solution was initially a black slurry but it turned transparent as complex was produced. After 2 hours, a colorless, transparent solution was obtained. The resultant solution was filtered with a 0.45 micron membrane filter and the solvent was removed at vacuum to obtain white solid. The solid was dried and weighed to obtain 3.96 g of a silver complex (yield=77.19%). Most of the silver complex was decomposed below 130° C. to leave metallic silver and the silver content was 23.48 wt % (TGA analysis).

Example 41

Reaction of Silver Oxide with 2-ethylhexylammonium 2-ethylhexylcarbonate

Into a 50 mL Schlenk flask equipped with a stirrer were added 4.13 g (12.90 mmol) of 2-ethylhexylammonium 2-ethylhexylcarbonate (viscous liquid) and 1.0 g (4.31 mmol) of silver oxide. The reaction solution was initially a black slurry but it turned transparent as complex was produced. After 2 hours, a yellow, transparent solution was obtained. The resultant solution was filtered with a 0.45 micron membrane filter and the solvent was removed at vacuum to obtain white solid. The solid was dried and weighed to obtain 3.96 g of a silver complex (yield=77.19%). Most of the silver complex was decomposed below 130° C. to leave metallic silver and the silver content was 23.48 wt % (TGA analysis).

Example 42

Reaction of Silver Oxide with Aminoethylammonium Aminoethylcarbonate

In a 50 mL Schlenk flask equipped with a stirrer, 2.35 g (12.90 mmol) of aminoethylammonium aminoethylcarbonate (white solid) was dissolved in 10 mL of methanol and 1.0 g (4.31 mmol) of silver oxide was added. The reaction solution was initially a black slurry but it turned transparent as complex was produced. After 2 hours, a colorless, transparent solution was obtained. The resultant solution was filtered with a 0.45 micron membrane filter and the solvent was removed at vacuum to obtain black, viscous liquid. The liquid was dried and weighed to obtain 2.42 g of a silver complex (yield=72.23%). Most of the silver complex was decomposed below 130° C. to leave metallic silver and the silver content was 38.45 wt % (TGA analysis).

Example 43

Reaction of Silver Oxide with 2-ethylhexylammonium 2-ethylhexylcarbonate and Aminoethylammonium Aminoethylcarbonate In a 50 mL Schlenk flask equipped with a stirrer, 3.87 g (12.9 mmol) of a 6:1 (molar ratio) mixture of 2-ethylhexylammonium 2-ethylhexylcarbonate and aminoethylammonium aminoethylcarbonate was dissolved in 10 mL of methanol and 1.0 g (4.31 mmol) of silver oxide was added. The reaction solution was initially a black slurry but it turned transparent as complex was produced. After 2 hours of reaction, a colorless, transparent solution was obtained. The resultant solution was filtered with a 0.45 micron membrane filter and the solvent was removed at vacuum to obtain orange, viscous liquid. The liquid was dried and weighed to obtain 3.05 g of a silver complex (yield=78.85%). Most of the silver complex was decomposed below 130° C. to leave metallic silver. The silver content was 30.41 wt % (TGA analysis).

Example 44

Reaction of Silver Sulfate with 2-ethylhexylammonium 2-ethylhexylcarbonate

In a 50 mL Schlenk flask equipped with a stirrer, 3.07 g (9.60 mmol) of 2-ethylhexylammonium 2-ethylhexylcarbonate (viscous liquid) was dissolved in 10 mL of methanol and 1.0 g (3.2 mmol) of silver sulfate was added. The reaction solution was initially a white slurry but it turned transparent as complex was produced. After 2 hours, a completely transparent solution was obtained. The resultant solution was filtered with a 0.45 micron membrane filter and the solvent was removed at vacuum to obtain white solid. The solid was recrystallized in ethyl acetate, dried and weighed to obtain 3.55 g of a silver complex (yield=87.2%). Most of the silver complex was decomposed below 130° C. to leave metallic silver and the silver content was 19.52 wt % (TGA analysis).

Example 45

Reaction of Silver Nitrate with 2-ethylhexylammonium 2-ethylhexylcarbonate

In a 50 mL Schlenk flask equipped with a stirrer, 2.84 g (8.86 mmol) of 2-ethylhexylammonium 2-ethylhexylcarbonate (viscous liquid) was dissolved in 10 mL of methanol and 1.0 g (5.9 mmol) of silver nitrate was added. The reaction solution was initially a white slurry but it turned transparent as complex was produced. After 2 hours, a completely transparent solution was obtained. The resultant solution was filtered with a 0.45 micron membrane filter and the solvent was removed at vacuum to obtain white solid. The solid was recrystallized in ethyl acetate, dried and weighed to obtain 3.12 g of a silver complex (yield=81.34%). Most of the silver complex was decomposed below 130° C. to leave metallic silver and the silver content was 19.88 wt % (TGA analysis).

Example 46

Reaction of Silver Cyanide with 2-ethylhexylammonium 2-ethylhexylcarbonate

In a 50 mL Schlenk flask equipped with a stirrer, 3.59 g (11.20 mmol) of 2-ethylhexylammonium 2-ethylhexylcarbonate (viscous liquid) was dissolved in 10 mL of methanol and 1.0 g (7.5 mmol) of silver cyanide was added. The reaction solution was initially a white slurry but it turned transparent as complex was produced. After 2 hours, a completely transparent solution was obtained. The resultant solution was filtered with a 0.45 micron membrane filter and the solvent was removed at vacuum to obtain white solid. The solid was recrystallized in ethyl acetate, dried and weighed to obtain 3.93 g of a silver complex (yield=85.62%). Most of the silver complex was decomposed below 130° C. to leave metallic silver and the silver content was 20.37 wt % (TGA analysis).

From the silver contents of the prepared compounds, m values were calculated. They are given in Table 1 below.

TABLE 1

| Example No. | m value |
|---|---|
| 1 | 1.3 |
| 2 | 1.1 |
| 3 | 1.1 |
| 4 | 1.1 |
| 5 | 1.2 |
| 6 | 1.2 |
| 7 | 1.6 |
| 8 | 1.0 |
| 9 | 1.1 |
| 10 | 1.4 |
| 11 | 1.1 |
| 12 | 1.1 |
| 13 | 1.9 |
| 14 | 1.6 |
| 15 | 1.0 |
| 16 | 1.0 |
| 17 | 1.0 |
| 18 | 0.9 |
| 19 | 0.7 |
| 20 | 1.3 |
| 21 | 1.2 |
| 22 | 1.1 |
| 23 | 1.2 |
| 24 | 2.1 |

TABLE 1-continued

| Example No. | m value |
|---|---|
| 25 | 1.0 |
| 26 | 1.3 |
| 27 | 1.5 |
| 28 | 1.6 |
| 29 | 1.3 |
| 30 | 1.2 |
| 31 | 1.6 |
| 32 | 1.5 |
| 33 | 1.8 |
| 34 | 2.5 |
| 35 | 1.8 |
| 36 | 2.0 |
| 37 | 2.2 |
| 38 | 1.6 |
| 39 | 1.1 |
| 40 | 1.1 |
| 41 | 1.1 |
| 42 | 1.0 |
| 43 | 0.8 |
| 44 | 1.4 |
| 45 | 1.4 |
| 46 | 1.3 |
| — | — |
| — | — |

Example 47

4 g of the silver complex prepared in Example 1 was dissolved in 5 g of butyl alcohol. After adjusting the viscosity to 500 cps, pattering was performed on a coated paper (ITP20HPG or ITP20SPH; InkTec) on a silk screen patterned to 320 meshes using a stainless steel (SUS) wire cloth. After heat treatment at 100° C. for 5 minutes and then at 130° C. for 10 minutes, a metal pattern having a conductivity of 400-500 mΩ/□ was obtained.

Example 48

4 g of the silver complex prepared in Example 1 was dissolved in 10 g of isopropyl alcohol. After adjusting the viscosity to 13 cps, pattering was performed on a PET film for one time using an ink-jet printer. After heat treatment at 80° C. for 5 minutes and then at 130° C. for 10 minutes, a metal pattern having a conductivity of 200-300 mΩ/□ was obtained.

Example 49

4 g of the silver complex prepared in Example 23 was dissolved in 5 g of 2-hexyl alcohol. After adjusting the viscosity to 500 cps, pattering was performed on a coated paper (ITP20HPG or ITP20SPH; InkTec) on a 320-mesh patterned silk screen. After heat treatment at 100° C. for 5 minutes and then at 130° C. for 10 minutes, a metal pattern having a conductivity of 400-500 mΩ/□ was obtained.

Example 50

4 g of the silver complex prepared in Example 24 was dissolved in 10 g of butyl alcohol. After adjusting the viscosity to 13 cps, pattering was performed on a PET film for one time using an ink-jet printer. After heat treatment at 80° C. for 5 minutes and then at 130° C. for 10 minutes, a metal pattern having a conductivity of 200-300 mΩ/□ was obtained.

INDUSTRIAL APPLICABILITY

The present invention provides a useful organic silver complex by reacting the silver compound represented by the formula 2 with the ammonium carbamate compound or the ammonium carbonate compound represented by the formula 3, 4 or 5.

As the TGA analysis shows, the organic silver complex of the present invention is decomposed at a very low temperature to give pure metal film or powder. So, it can be processed into a variety of metallic silver films or formed into an ultrathin film by deposition under high vacuum. Thus, it can be used in plating, medicine, photography, electricity and electronics, fibers, detergents, household appliances, organics and polymer synthesis as catalyst or may be used in preparation of silver powder, paste and nanoparticle. Particularly, it may be utilized in low-resistance metal wirings, printed circuit boards (PCB), flexible printed circuit boards (FPC), antennas for radio frequency identification (RFID) tags, plasma display panels (PDP), liquid crystal displays (TFT-LCD), organic light emitting diodes (OLED), flexible displays, organic thin-film transistors (OTFT), electrodes, etc. as precursor material for metal patterning by chemical vapor deposition (CVD), plasma vapor deposition, sputtering, electroplating, lithography, electron beam, laser, etc. In addition, the organic silver complex solution of the present invention may be spin coated, roll coated, spray coated, dip coated, flow coated, ink-jet printed, offset printed, screen printed, gravure printed or flexo printed on such a substrate as glass, silicon wafer and polymer film like polyester or polyimide, paper, etc. and reduced, oxidized or heat-treated to form a metal or metal oxide pattern.

While the present invention has been described in detail with reference to the preferred embodiments, those skilled in the art will appreciate that various modifications and substitutions can be made thereto without departing from the spirit and scope of the present invention as set forth in the appended claims.

The invention claimed is:

1. A method for preparing a silver complex by reacting silver oxide with a mixture of ammonium carbamate and isopropyl amine at room temperature in the presence of methanol.

* * * * *